US006906026B1

(12) United States Patent
Noble et al.

(10) Patent No.: US 6,906,026 B1
(45) Date of Patent: Jun. 14, 2005

(54) METHODS FOR TREATING CONDITIONS ASSOCIATED WITH THE ACCUMULATION OF EXCESS EXTRACELLULAR MATRIX

(75) Inventors: Nancy A. Noble, Salt Lake City, UT (US); Wayne A. Border, Salt Lake City, UT (US)

(73) Assignee: The University of Research Foundation, Salt Lake City, UT (US)

(*) Notice: Subject to any disclaimer, the term of this patent is extended or adjusted under 35 U.S.C. 154(b) by 380 days.

(21) Appl. No.: 09/869,820

(22) PCT Filed: Jul. 5, 2000

(86) PCT No.: PCT/US00/00179

§ 371 (c)(1),
(2), (4) Date: Jul. 5, 2001

(87) PCT Pub. No.: WO00/40227

PCT Pub. Date: Jul. 13, 2000

Related U.S. Application Data

(60) Provisional application No. 60/114,795, filed on Jan. 5, 1999.

(51) Int. Cl.[7] ...................... A61K 48/00; A61K 39/395; A61K 38/00
(52) U.S. Cl. ................... 514/2; 514/4; 514/44; 435/4; 435/6; 435/7.1
(58) Field of Search ....................... 514/2, 4, 44; 435/4, 435/6, 7.1

(56) References Cited

U.S. PATENT DOCUMENTS

| 5,571,714 A | 11/1996 | Dasch et al. |
| 5,824,655 A | * 10/1998 | Border .......................... 514/44 |
| 6,316,258 B1 | * 11/2001 | Noble et al. ................. 435/375 |

FOREIGN PATENT DOCUMENTS

| WO | WO91/04748 | 4/1991 |
| WO | WO93/09800 | 5/1993 |
| WO | WO93/10808 | 6/1993 |
| WO | WO96/25178 | 8/1996 |
| WO | WO97/39028 | 10/1997 |
| WO | WO99/34823 | 7/1999 |

OTHER PUBLICATIONS

Moll et al., Kidney International, vol. 48: 1459–1468, 1995.*
Abboud, Hanna E., "Platelet–derived growth factor and mesangial cells," *Kidney International*, 41:581–3, 1992 (Exhibit 8).
Anderson, Sharon et al., "Control of Glomerular Hypertension Limits Glomerular Injury in Rats with Reduced Renal Mass," *The Journal of Clinical Investigation*, 76:612–9, 1985 (Exhibit 9).
Antonipillai, I. et al., "Transforming growth factor–β is a renin secretagogue at picomolar concentrations," *American Journal of Physiology*, 265:F537–41, 1993 (Exhibit 10).

Arai, N. et al., "Complete Nucleotide Sequence of the Chromosomal Gene for Human IL–4 and Its Expression," *Journal of Immunology*, 142:274–82, 1989 (Exhibit 11).
Arai, Makoto et al., "In Vivo Transfection of Genes for Renin and Angiotensinogen into the Glomerular Cells Induced Phenotypic Change of the Mesangial Cells and Glomerular Sclerosis," *Biochemical and Biophysical Research Communications*, 206:525–32, 1995 (Exhibit 12).
Armelin, Hugo A., "Pituitary Extracts and Steroid Hormones in the Control of 3T3 Cell Growth (mouse fibroblasts/growth factor)," *Proceedings of the National Academy of Sciences USA*, 70:2702–6, 1973 (Exhibit 13).
Arnheim, Norman and Henry Erlich, "Polymerase Chain Reaction Strategy," *Annual Review of Biochemistry*, 61:131–56, 1992 (Exhibit 14).
Badasso, M. et al., "Crystallization and Preliminary X–ray Analysis of Complexes of Peptide Inhibitors with Human Recombinant and Mouse Submandibular Renins," *Journal of Molecular Biology*, 223:447–53, 1992 (Exhibit 15).
Bagchus, W. M. et al., "Glomerulonephritis Induced by Monoclonal Anti–Thy 1.1 Antibodies," *Laboratory Investigation*, 55:680–7, 1986 (Exhibit 16).
Chakraborty, Asit K. et al., "Synthetic retrotransposon vectors for gene therapy," *FASEB Journal*, 7:971–7, 1993 (Exhibit 35).
Chansel, Dominique et al., "Identification and regulation of renin in human cultured mesangial cells," *American Journal of Physiology*, 252:F32–8, 1987 (Exhibit 36).
Ciccarone, Valentina C. et al., "Identification of Enhancer–like Elements in Human IFN–γ Genomic DNA," *Journal of Immunology*, 144:725–30, 1990 (Exhibit 37).
Coffin, in Weiss et al. (Eds.), RNA Tumor Viruses, 2nd Ed., vol. 2, Cold Spring Laboratory, NY, pp. 17–73, 1985 (Exhibit 38).
Cole, S. P. C. et al., "The EBV–Hybridoma Technique and Its Application to Human Lung Cancer," *Monoclonal Antibodies and Cancer Therapy*, Alan R. Liss, Inc. 77–96, 1985 (Exhibit 39).
Compagnon, B. et al., "Targeting of Poly(rl)–Poly(rC) by Fusogenic (F Protein) Immunoliposomes," *Experimental Cell Research*, 200:333–8, 1992 (Exhibit 40).
Cook, R. Frank et al., "Retrotransposon Gene Engineering," *Biotechnology*, 9:748–51, 1991 (Exhibit 41).

(Continued)

*Primary Examiner*—Sean McGarry
(74) *Attorney, Agent, or Firm*—Mandel & Adriano

(57) ABSTRACT

The present invention is methods and compositions for reducing and preventing the excess accumulation of extracellular matrix in a tissue and/or organ or at a wound site using a combination of agents that inhibit TGFβ, or using agents that inhibit TGFβ in combination with agents that degrade excess accumulated extracellular matrix. The compositions and methods of the invention are used to treat conditions such as fibrotic diseases and scarring that result from excess accumulation of extracellular matrix, impairing tissue or organ function or skin appearance in a subject.

20 Claims, 13 Drawing Sheets

OTHER PUBLICATIONS

Cote, Richard J. et al., "Generation of human monoclonal antibodies reactive with cellular antigens," *Proceedings of the National Academy of Sciences USA*, 80:2026–30, 1983 (Exhibit 42).

DePamphilis, M. L. et al., "Microinjecting DNA into Mouse Ova to Study DNA Replication and Gene Expression and to Produce Transgenic Animals," *BioTechniques*, 6:662–80, 1988 (Exhibit 43).

Dhanaraj, V. et al., "X–ray analyses of peptide–inhibitor complexes define the structural basis of specificity for human and mouse renins," *Nature*, 357:466–72, 1992 (Exhibit 44).

Dostal, David E. et al., "An Improved Method for Absolute Quantification of mRNA Using Multiplex Polymerase Chain Reaction: Determination of Renin and Angiotensinogen mRNA Levels in Various Tissues," *Analytical Biochemistry*, 223:239–50, 1994 (Exhibit 45).

Dzau, Victor J. and Jeffrey Kreisberg, "Cultured Glomerular Mesangial Cells Contain Renin: Influence of Calcium and Isoproterenol," *Journal of Cardiovascular Pharmacology*, 8:S6–10, 1986 (Exhibit 46).

Eltayeb, B. O. et al., "Effects of captopril on serum levels of TGF–$\beta$ in insulin–dependent diabetic patients," *Journal of the American Society of Nephrology*, 8:AO524, 1997 (Exhibit 47).

Felgner, Philip L. et al., "Lipofection: A highly efficient, lipid–mediated DNA–transfection procedure," *Proceedings of the National Academy of Sciences USA*, 84:7413–7, 1987 (Exhibit 48).

Felgner, P. L. et al., "Cationic Liposome Mediated Transfection," *Proceedings of the Western Pharmacology Society*, 32:115–21, 1989 (Exhibit 49).

Felgner, P. L. and G. Rhodes, "Gene therapeutics," *Nature*, 349:351–2, 1991 (Exhibit 50).

Fischli, Walter et al., "Ro 42–5892 is a Potent Orally Active Renin Inhibitor in Primates," *Hypertension*, 18:22–31, 1991 (Exhibit 51).

Flaumenhaft, Robert et al., "Activation of Latent Transforming Growth Factor $\beta$," *Advances in Pharmacology*, 24:51–76, 1993 (Exhibit 52).

Fujita, Takashi et al., "Regulation of Human Interleukin–2 Gene: Functional DNA Sequences in the 5' Flanking Region for the Gene Expression in Activated T Lymphocytes," *Cell*, 46:401–7, 1986 (Exhibit 53).

Baricos, William H. et al., "ECM degradation by cultured human mesangial cells is mediated by a PA/plasmin/MMP–2 cascade," *Kidney International*, 47:1039–47, 1995 (Exhibit 17).

Baricos, William H. et al. "Transforming Growth Factor–$\beta$ is a Potent Inhibitor of Extracellular Matrix Degradation by Cultured Human Mesangial Cells," *Journal of the American Society of Nephrology*, 10:790–5, 1999 (Exhibit 18).

Beaucage, S. L. and M. H. Caruthers, "Deoxynucleoside Phosphoramidites—A New Class of Key Intermediates for Deoxypolynucleotide Synthesis," *Tetrahedron Letters*, 22:1859–62, 1981 (Exhibit 19).

Bennett, C. Frank et al., "Cationic Lipids Enhance Cellular Uptake and Activity of Phosphorothioate Antisense Oligonucleotides," *Molecular Pharmacology*, 41:1023–33, 1992 (Exhibit 20).

Bongartz, Jean–Pierre et al., "Improved biological activity of antisense oligonucleotides conjugated to a fusogenic peptide," *Nucleic Acids Research*, 22:4681–8, 1994 (Exhibit 21).

Border, Wayne A. and Nancy A. Noble, "Transforming Growth Factor $\beta$ in Tissue Fibrosis," *New England Journal of Medicine*, 331:1286–92, 1994 (Exhibit 22).

Border, Wayne A. and Nancy A. Noble, "TGF–$\beta$ in kidney fibrosis: A target for gene therapy," *Kidney International*, 51:1388–96, 1997 (Exhibit 23).

Border, Wayne A. and Nancy A. Noble, "TGF–$\beta$," *Scientific American Science & Medicine*, 2:68–77, 1995 (Exhibit 24).

Border, Wayne A. and Nancy A. Noble, "Evidence that TGF–$\beta$ should be a therapeutic target in diabetic nephropathy," *Kidney International*, 54:1390–1, 1998 (Exhibit 25).

Border, Wayne A. and Nancy A. Noble, "Interactions of Transforming Growth Factor–$\beta$ and Angiotensin II in Renal Fibrosis," *Hypertension*, 31:181–8, 1998 (Exhibit 26).

Border, Wayne A. and Erkki Ruoslahti, "Transforming Growth Factor–$\beta$ in Disease: The Dark Side of Tissue Repair," *Journal of Clinical Investigation*, 90:1–7, 1992 (Exhibit 27).

Border, Wayne A. et al. "Suppression of experimental glomerulonephritis by antiserum against transforming growth factor $\beta 1$," *Nature*, 346:371–4, 1990 (Exhibit 28).

Border, Wayne A. et al., "Natural inhibitor of transforming growth factor–$\beta$ protects against scarring in experimental kidney disease," *Nature*, 360:361–4, 1992 (Exhibit 29).

Border, Wayne A. et al., "Transforming growth factor–$\beta$ regulates production of proteoglycans by mesangial cells," *Kidney International*, 37:689–95, 1990 (Exhibit 30).

Boshart, Michael et al., "A Very Strong Enhancer is Located Upstream of an Immediate Early Gene of Human Cytomegalovirus," *Cell*, 41:521–30, 1985 (Exhibit 31).

Boutorine, A. S. and E. V. Kostina, "Reversible covalent attachment of cholesterol to oligodeoxyribonucleotides for studies of the mechanisms of their penetration into eucaryotic cells," *Biochimie*, 75:35–41, 1993 (Exhibit 32).

Campbell, Duncan J. and Anthony J. Valentijn, "Identification of vascular renin–binding proteins by chemical cross–linking: inhibition of binding of renin by renin inhibitors," *Journal of Hypertension*, 12:879–90, 1994 (Exhibit 33).

Capaccioli, Sergio et al., "Cationic Lipids Improve Antisense Oligonucleotide Uptake and Prevent Degradation in Cultured Cells and in Human Serum," *Biochemical and Biophysical Research Communications*, 197:818–25, 1993 (Exhibit 34).

Gibbons, Gary H. et al., "Vascular Smooth Muscle Cell Hypertrophy vs. Hyperplasia," *Journal of Clinical Investigation*, 90:456–61, 1992 (Exhibit 54).

Grainger, David J. et al., "The serum concentration of active transforming growth factor–$\beta$ is severely depressed in advanced atherosclerosis," *Nature Medicine*, 1:74–9, 1995 (Exhibit 55).

Greene, E. L. et al., "Role of Aldosterone in the Remnant Kidney Model in the Rat," *Journal of Clinical Investigation*, 98:1063–8, 1996 (Exhibit 56).

Gupta, Prem et al., "Transforming Growth Factor–$\beta 1$ Inhibits Aldosterone and Stimulates Adrenal Renin in Cultured Bovine Zona Glomerulosa Cells," *Endocrinology*, 131:631–6, 1992 (Exhibit 57).

Haensler, Jean and Francis C. Szoka, Jr., "Polyamidoamine Cascade Polymers Mediate Efficient Transfection of Cells in Culture," *Bioconjugate Chem*, 4:372–9, 1993 (Exhibit 58).

Haraguchi, Masashi et al., "Recombinant Tissue Type Plasminogen Activator (rt–PA) Promotes Glomerular Plasmin Generation and Extracellular Matrix (ECM) Turnover in Anti–Thy–1 Nephritis," *Journal of the American Society of Nephrology*, 9:A2639, 1998 (Exhibit 59).

Horikoshi, Satoshi et al., "Water Deprivation Stimulates Transforming Growth Factor–β2 Accumulation in the Juxtaglomerular Apparatus of Mouse Kidney," *Journal of Clinical Investigation*, 88:2117–22, 1991 (Exhibit 60).

Huse, William D. et al., "Generation of a Large Combinatorial Library of the Immunoglobulin Repertoire in Phage Lambda," *Science*, 246:1275–81, 1989 (Exhibit 61).

Husted, Russell F. et al., "Induction of resistance to mineralocorticoid hormone in cultured inner medullary collecting duct cells by TGF–β1," *American Journal of Physiology*, 267:F767–75, 1994 (Exhibit 62).

Huxley, Clare, "Mammalian artificial chromosomes: a new tool for gene therapy," *Gene Therapy*, 1:7–12, 1994 (Exhibit 63).

Huxley, Clare et al., "Ordering Up Big MACs," *BioTechnology*, 12:586–90, 1994 (Exhibit 64).

Isaka, Yoshitaka et al., "Gene therapy by skeletal muscle expression of decorin prevents fibrotic disease in rat kidney," *Nature Medicine*, 2:418–23, 1996 (Exhibit 65).

Isaka, Yoshitaka et al., "Glomerulosclerosis Induced by In Vivo Transfection of Transforming Growth Factor–β or Platelet–derived Growth Factor Gene into the Rat Kidney," *Journal of Clinical Investigation*, 92:2597–601, 1993 (Exhibit 66).

Isaka, Y. et al., "Decorin Gene Therapy for Experimental Glomerulonephritis," *Journal of the American Society of Nephrology*, 6:1261, 1995 (Exhibit 67).

Isaka, Yoshitaka et al., "Gene therapy by transforming growth factor–β receptor–IgG Fc chimera suppressed extracellular matrix accumulation in experimental glomerulonephritis," *Kidney International*, 55:465–75, 1999 (Exhibit 68).

Johnson, Richard J. et al., "The Activated Mesangial Cell: A Glomerular "Myofibroblast"?", *Journal of the American Society of Nephrology*, 2:S190–7, 1992 (Exhibit 69).

Kagami, Shoji et al., "Angiotensin II Stimulates Extracellular Matrix Protein Synthesis through Induction of Transforming Growth Factor–β Expression in Rat Glomerular Mesangial Cells," *Journal of Clinical Investigation*, 93:2431–7, 1994 (Exhibit 70).

Kagami, Shoji et al., "Coordinated Expression of β1 Integrins and Transforming Growth Factor–β–Induced Matrix Proteins in Glomerulonephritis," *Laboratory Investigation*, 69:68–76, 1993 (Exhibit 71).

Kanai, Hidetoshi et al., "Angiotensin II upregulates the expression of TGF–β type I and type II receptors," *Journal of the American Society of Nephrology*, 8:A2410, 1997 (Exhibit 72).

Karlsson, Stefan et al., "Transfer of genes into hematopoietic cells using recombinant DNA viruses," *Proceeding of the National Academy of Sciences USA*, 82:158–62, 1985 (Exhibit 73).

Karlsson, Stefan et al., "Stable gene transfer and tissue–specific expression of a human globin gene using adenoviral vectors," *EMBO Journal*, 5:2377–85, 1986 (Exhibit 74).

Kashgarian, Michael and R. Bernd Sterzel, "The pathobiology of the mesangium," *Kidney International*, 41:524–9, 1992 (Exhibit 75).

Kim, Seong–Jin et al., "Post–transcriptional Regulation of the Human Transforming Growth Factor–β1 Gene," *Journal of Biological Chemistry*, 267:13702–7, 1992 (Exhibit 76).

Kirschmeier, Paul T. et al., "Construction and Characterization of a Retroviral Vector Demonstrating Efficient Expression of Cloned cDNA Sequences," *DNA*, 7:219–25, 1988 (Exhibit 77).

Kitamura, Masanori et al., "Transfer of a mutated gene encoding active transforming growth factor–β1 suppresses mitogenesis and IL–1 response in the glomerulus," *Kidney International*, 48:1747–57, 1995 (Exhibit 78).

Klahr, Saulo et al., "The Progression of Renal Disease," *New England Journal of Medicine*, 318:1657–66, 1988 (Exhibit 79).

Köhler, G. and C. Milstein, "Continuous cultures of fused cells secreting antibody of predefined specificity," *Nature*, 256:495–7, 1975 (Exhibit 80).

Kozbor, Danuta and John C. Roder, "The production of monoclonal antibodies from human lymphocytes," *Immunology Today*, 4:72–79, 1983 (Exhibit 81).

Kulkarni, Ashok B. et al., "Transforming growth factor β1 null mutation in mice causes excessive inflammatory response and early death," *Proceedings of the National Academy of Sciences USA*, 90:770–4, 1993 (Exhibit 82).

Lawrence, Daniel A. et al., "Structure–Function Studies of the SERPIN Plasminogen Activator Inhibitor Type 1," *Journal of Biological Chemistry*, 265:20293–301, 1990 (Exhibit 83).

Lawrence, Daniel A. et al., "Localization of Vitronectin Binding Domain in Plasminogen Activator Inhibitor–1," *Journal of Biological Chemistry*, 269:15223–8, 1994 (Exhibit 84).

Lawrence, Daniel A. et al., "Characterization of the Binding of Different Conformational Forms of Plasminogen Activator Inhibitor–1 to Vitronectin," *Journal of Biological Chemistry*, 272:7676–80, 1997 (Exhibit 85).

Lawrence, Daniel A., "The Role of Reactive–Center Loop Mobility in the Serpin Inhibitory Mechanism," *Advances in Experimental Medicine and Biology*, 425:99–108, 1997 (Exhibit 86).

Leonetti, Jean–Paul et al., "Biological Activity of Oligonucleotide–Poly(L–lysine) Conjugates: Mechanism of Cell Uptake," *Bioconjugate Chem.*, 1:149–53, 1990 (Exhibit 87).

Leonetti, Jean–Paul et al., "Antibody–targeted liposomes containing oligodeoxyribonucleotides complementary to viral RNA selectively inhibit viral replication," *Proceedings of the National Academy of Sciences*, 87:2448–51, 1990 (Exhibit 88).

Letterio, John J. et al., "Maternal Rescue of Transforming Growth Factor–β1 Null Mice," *Science*, 264:1936–8, 1994 (Exhibit 89).

Linsley, Peter S. et al., "T–cell antigen CD28 mediates adhesion with B cells by interacting with activation antigen B7/BB–1,"0 *Proceedings of the National Academy of Sciences USA*, 87:5031–5, 1990 (Exhibit 90).

Lopez–Armada, M. J. et al., "Immune Complexes Stimulate the Expression and Synthesis of Matrix Proteins in Cultured Rat and Human Mesangial Cells Role of Transforming Growth Factor β," *Journal of the American Society of Nephrology*, 5:67P, 1994 (Exhibit 91).

Mann, Richard et al., "Construction of a Retrovirus Packaging Mutant and Its Use to Produce Helper–Free Defective Retrovirus," *Cell*, 33:153–9, 1983 (Exhibit 92).

Markowitz, Sanford et al., "Inactivation of the Type II TGF–β Receptor in Colon Cancer Cells with Microsatellite Instability," *Science*, 268:1336–8, 1995 (Exhibit 93).

Marshall, Bruce C. et al., "Alveolar Epithelial Cell Plasminogen Activator," *Journal of Biological Chemistry*, 265:8198–204, 1990 (Exhibit 94).

Mathews, Salima et al., "Recombinant Human Renin Produced in Different Expression Systems: Biochemical Properties and 3D Structure," *Protein Expression and Purification*, 7:81–91, 1996 (Exhibit 95).

Matteucci, M. D. and M. H. Caruthers, "Synthesis of Deoxyoligonucleotides on a Polymer Support," *Journal of the American Chemical Society*, 103:3185–91, 1981 (Exhibit 96).

Miller, A. Dusty and Carol Buttimore, "Redesing of Retrovirus Packaging Cell Lines to Avoid Recombination Leading to Helper Virus Production," *Molecular and Cellular Biology*, 6:2895–902, 1986 (Exhibit 97).

Miyatake, S. et al., "Structure of the chromosomal gene for granulocyte–macrophage colony stimulating factor: comparison of the mouse and human genes," *EMBO Journal*, 4:2561–8, 1985 (Exhibit 98).

Morishita, Ryuichi et al., "Single intraluminal delivery of antisense cdc2 kinase and proliferating–cell nuclear antigen oligonucleotides results in chronic inhibition of neointimal hyperplasia," *Proceedings of the National Academy of Sciences USA*, 90:8474–8, 1993 (Exhibit 99).

Moss, Bernard, "Vaccinia and other poxvirus expression vectors," *Current Opinion in Biotechnology*, 3:518–22, 1992 (Exhibit 100).

Naviaux, Robert K. and Inder M. Verma, "Retroviral vectors for persistent expression in vivo," *Current Opinion in Biotechnology*, 3:540–7, 1992 (Exhibit 101).

Nedwin, Glenn E. et al, "Human lymphotoxin and tumor necrosis factor genes: structure, homology and chromosomal localization," *Nucleic Acids Research*, 13:6361–73, 1985 (Exhibit 102).

Nguyen, Geneviève et al, "Specific receptor binding of renin on human mesangial cells in culture increases plasminogen activator inhibitor–1 antigen," *Kidney International*, 50:1897–903, 1996 (Exhibit 103).

Noble, Nancy A. and Wayne A. Border, "Angiotensin II in Renal Fibrosis: Should TGF–β Rather Than Blood Pressure be the Therapeutic Target?," *Seminars in Nephrology*, 17:455–66, 1997—Exhibit 104).

Ohno, Minoru et al., "Fluid Shear Stress Induces Endothelial Transforming Growth Factor Beta–1 Transcription and Production," *Journal of Clinical Investigation*, 95:1363–9, 1995 (Exhibit 105).

Okuda, Seiya et al., "Elevated Expression of Transforming Growth Factor–β and Proteoglycan Production in Experimental Glomerulonephritis," *Journal of Clinical Investigation*, 86:453–62, 1990 (Exhibit 106).

Peten, Emmanuel P. et al., "The Contribution of Increased Collagen Synthesis to Human Glomerulosclerosis: A Quantitative Analysis of α2IV Collagen mRNA Expression by Competitive Polymerase Chain Reaction," *Journal of Experimental Medicine*, 176:1571–6, 1992 (Exhibit 107).

Peters, Harm et al., "Therapeutic reduction of TGF–β and matrix proteins in Thy 1–induced glomerulonephritis is enhanced by angiotensin blockade at higher doses and further enhanced by addition of low protein diet," *Journal of the American Society of Nephrology*, 8:A2438, 1997 (Exhibit 108).

Peters, H. et al., "Angiotensin II Blockade Reduces Glomerular Transforming Growth Factor β and Matrix Protein Synthesis in Undiseased Rats," *Kidney & Blood Pressure Research*, 21:131–2, 1998 (Exhibit 109).

Peters, Harm et al., "Targeting TGF–β overexpression in renal disease: Maximizing the antifibrotic action of angiotensin II blockade," *Kidney International*, 54:1570–80, 1998 (Exhibit 110).

Price, Jack et al., "Lineage analysis in the vertebrate nervous system by retrovirus–mediated gene transfer," *Proceedings of the National Academy of Sciences USA*, 84:156–60, 1987 (Exhibit 111).

Rahuel, Joseph et al., "The Crystal Structures of Recombinant Glycosylated Human Renin Alone and in Complex with a Transition State Analog Inhibitor," *Journal of Structural Biology*, 107:227–36, 1991 (Exhibit 112).

Rajaonarivony, M. et al., "Development of a New Drug Carrier Made from Alginate," *Journal of Pharmaceutical Sciences*, 82:912–7, 1993 (Exhibit 113).

Ray, Patricio E. et al., "Renal vascular induction of TGF–β2 and renin by potassium depletion," *Kidney International*, 44:1006–13, 1993 (Exhibit 114).

Ray, Patricio E. et al., "Modulation of Renin Release and Renal Vascular Smooth Muscle Cell Contractility by TGF–β2," *Progression of Chronic Renal Diseases*, 118:238–48, 1996 (Exhibit 115).

Remuzzi, Giuseppe et al., "Understanding the nature of renal disease progression," *Kidney International*, 51:2–15, 1997 (Exhibit 116).

Remuzzi, Giuseppe and Norberto Perico, "Protecting Single–Kidney Allografts from Long–Term Functional Deterioration," *Journal of the American Society of Nephrology*, 9:1321–32, 1998 (Exhibit 117).

Riser, Bruce L. et al., "Intraglomerular Pressure and Mesangial Stretching Stimulate Extracellular Matrix Formation in the Rat," *Journal of the Clinical Investigation*, 90:1932–43, 1992 (Exhibit 118).

Riser, Bruce L. et al., "Mesangial Cell (MC) Stretch Stimulates the Secretion and Activation of Transforming Growth Factor Beta 1 (TGF–β1) But Not TGF–β2/TGF–β3," *Journal of the American Society of Nephrology*, 4:67P, 1993 (Exhibit 119).

Rocco, Michael V. et al., "Elevated glucose stimulates TGF–β gene expression and bioactivity in proximal tubule," *Kidney International*, 41:107–14, 1992 (Exhibit 120).

Rondeau, E. et al., "Plasminogen activator inhibitor 1 in renal fibrin deposits of human nephropathies," *Clinical Nephrology*, 33:55–60, 1990 (Exhibit 121).

Rosenberg, Mark E. et al., "Effect of Dietary Protein on Rat Renin and Angiotensinogen Gene Expression," *Journal of Clinical Investigation*, 85:1144–9, 1990 (Exhibit 122).

Ruiz–Ortega, M. et al., "Platelet Activating Factor (PAF) Stimulates the Expression and Synthesis of Extracellular Matrix Proteins in Cultured Renal Cells," *Journal of the American Society of Nephrology*, 5:64P, 1994 (Exhibit 123).

Sahai, Atul et al., "Chronic Hypoxia Stimulates the Expression of Extracellular Matrix Proteins and TGF–β in Cultured Mesangial Cells," *Journal of the American Society of Nephrology*, 6:1877, 1995 (Exhibit 124).

Sealey, Jean E. et al., "Specific Prorenin / Renin Binding (ProBP): Identification and Characterization of a Novel Membrane Site," *American Journal of Hypertension*, 9:491–502, 1996 (Exhibit 125).

Sharma, Kumar et al., "Neutralization of TGF–β by Anti-TGF–β Antibody Attenuates Kidney Hypertrophy and the Enhanced Extracellular Matrix Gene Expression in STZ–Induced Diabetic Mice," *Diabetes*, 45:522–30, 1996 (Exhibit 126).

Shah, Mamta et al., "Control of scarring in adult wounds by neutralising antibody to transforming growth factor β," *The Lancet*, 339:213–4, 1992 (Exhibit 127).

Sherman, Patti M. et al., "Identification of Tissue–type Plasminogen Activator–specific Plasminogen Activator Inhibitor–1 Mutants," *Journal of Biological Chemistry*, 270:9301–6, 1995 (Exhibit 128).

Shoemaker, Sara G. et al., "Transcriptional regulation of interleukin 3 gene expression in T lymphocytes," *Proceedings of the National Academy of Sciences USA*, 87:9650–4, 1990 (Exhibit 129).

Shull, Marcia M. et al., "Targeted disruption of the mouse transforming growth factor–β1 gene results in multifocal inflammatory disease," *Nature*, 359:693–9, 1992 (Exhibit 130).

Sielecki, Anita R. et al., "Structure of Recombinant Human Renin, a Target for Cardiovascular–Active Drugs, at 2.5 Å Resolution," *Science*, 243:1346–51, 1989 (Exhibit 131).

Smith, Theodore A. G. et al., "Adenovirus mediated expression of therapeutic plasma levels of human factor IX in mice," *Nature Genetics*, 5:397–402, 1993 (Exhibit 132).

Tomooka, Suguru et al., "Glomerular matrix accumulation is linked to inhibition of the plasmin protease system," *Kidney International*, 42:1462–9, 1992 (Exhibit 133).

Uotila, Marjatta et al., "Two–Site Sandwich Enzyme Immunoassay with Monoclonal Antibodies to Human Alpha–Fetoprotein," *Journal of Immunological Methods*, 42:11–5, 1981 (Exhibit 134).

Véniant, Murielle et al., "Vascular Damage without Hypertension in Transgenic Rate Expressing Prorenin Exclusively in the Liver," *Journal of Clinical Investigation*, 98:1966–70, 1996 (Exhibit 135).

Wagner, Richard W., "Gene inhibition using antisense oligodeoxynucleotides," *Nature*, 372:332–5, 1994 (Exhibit 136).

Wagner, Richard W. et al., "Antisense Gene Inhibition by Oligonucleotides Containing C–5 Propyne Pyrimidines," *Science*, 260:1510–3, 1993 (Exhibit 137).

Wexler, Ruth R. et al., "Rationale for the Chemical Development of Angiotensin II Receptor Antagonists," *American Journal of Hypertension*, 5:209S–20S, 1992 (Exhibit 138).

Yei, Soonpin et al., "Adenovirus–mediated gene transfer for cystic fibrosis: quantitative evaluation of repeated in vivo vector administration to the lung," *Gene Therapy*, 1:192–200, 1994 (Exhibit 139).

Yu, C. Yung et al., "Cosmid Cloning and Walking to Map Human CD1 Leukocyte Differentiation Antigen Genes," *Methods of Enzymology*, 217:378–98, 1993 (Exhibit 140).

Zhu, Ning et al., "Systemic Gene Expression After Intravenous DNA Delivery into Adult Mice," *Science*, 261:209–11, 1993 (Exhibit 141).

Ziyadeh, Fuad N. et al., "Stimulation of Collagen Gene Expression and Protein Synthesis in Murine Mesangial Cells by High Glucose is Mediated by Autocrine Activation of Transforming Growth Factor–β," *Journal of Clinical Investigation*, 93:536–42, 1994 (Exhibit 142).

Moss, et al., "Roles of vaccinia virus in the development of new vaccines," *Vaccine*, 1988, 6:161–163. (Exhibit 144.

Zelphati, Olivier et al., "Inhibition of HIV–1 Replication in Cultured Cells with Antisense Oligonucleotides Encapsulated in Immunoliposomes," *Antisense and Research and Development*, 1993, 3:323–38 (Exhibit 145).

* cited by examiner

Effect of tPA on anti-Thy-1 nephritis at day 6

Plasmin activity of isolated glomeruli

*$P<0.01$ vs. normal
**$P<0.01$ vs. disease control
***$P<0.05$ vs. disease control

METHODS FOR TREATING CONDITIONS ASSOCIATED WITH THE ACCUMULATION OF EXCESS EXTRACELLULAR MATRIX

This application claims the priority of International Application No. PCT/US00/0179, filed Jan. 5, 2000, which claims the priority of U.S. Ser. No. 60/114,795, filed Jan. 5, 1999.

This invention was made with government support under Grant No. 5R01DK49374 and 2R37DK043609 awarded by the National Institute of Health. The government has certain rights to this invention.

FIELD OF THE INVENTION

This invention relates to a method for preventing or reducing excess accumulation of extracellular matrix in tissues or organs or at a wound site, and more particularly to the prevention and treatment of conditions resulting from excess accumulation of extracellular matrix, using a combination of agents that inhibit TGFβ, or a combination of agents that inhibit TGFβ and agents that degrade excess accumulated extracellular matrix.

BACKGROUND OF THE INVENTION

Excess deposition and accumulation of extracellular matrix (ECM) is found in diseases such as fibrosis of the kidney or lung. Although the cytokine transforming growth factor Beta (TGFβ) regulates extracellular matrix deposition for tissue repair, overproduction of TGFβ clearly underlies tissue fibrosis caused by excess deposition of extracellular matrix resulting in disease (Border and Ruoslahti, *J. Clin. Invest.* 90:1–7 (1992)). TGFβ's fibrogenic action results from simultaneous stimulation of matrix protein synthesis (Border et al., *Kidney Int* 37:689–695 (1990), inhibition of matrix degradation and turnover and enhanced cell-matrix interactions through modulation of integrin receptors that facilitate ECM assembly. Overproduction of TGFβ has been demonstrated in glomerulonephritis (Okuda et al., *J. Clin. Invest.* 86:453–462 (1990)), diabetic nephropathy and hypertensive glomerular injury and in related fibrotic disorders of the lung, liver, heart, arterial wall, skin, brain, joints and bone marrow (Border and Noble, *N. Eng. J. Med.* 331:128–1292 (1994)). In addition to the kidney, blocking the action of TGFβ with an agent such as antibody or the proteoglycan decorin has been shown to be therapeutic in fibrosis and scarring of the skin, lung, central nervous system and arterial wall (Border and Noble, *Kidney Int.* 51:1388–1396 (1997)).

Suppression of the production of ECM and prevention of excess accumulation of mesangial matrix in glomeruli of glomerulonephritic rats has been demonstrated by intravenous administration of neutralizing antibodies specific for TGFβ (Border et al., *Nature* 346:371–374 (1990)) or administration of purified decorin, a proteoglycan (Border et al., *Nature* 360:361–364 (1992)) and by introduction of nucleic acid encoding decorin, a TGFβ-inhibitory agent, into a rat model of acute mesangial glomerulonephritis (Isaka et al., *Nature Med.* 2:418–423 (1996)). Inhibition of TGFβ activity, using for example anti-TGFβ antibodies, has been shown to to disrupt TGFβ overproduction (Sharma et al., *Diabetes* 45:522–530 (1996)).

Dermal scarring following dermal injury results from excessive accumulation of fibrous tissue made up of collagen, fibronectin and proteoglycans at a wound site. Because the fibrous extracellular matrix lacks elasticity, scar tissue can impair essential tissue function as well as result in an undesirable cosmetic appearance. TGFβ is believed to induce the deposition of fibrous matrix at the wound site (Shah et al., *Lancet* 339:213–214 (1992)).

One explanation for persistent TGFβ overexpression in progressive fibrotic kidney disease is that repeated or multiple episodes of tissue injury, such as occurs in chronic diseases such as hypertension, diabetes or immune complex disease lead to continuous overproduction of TGFβ and extracellular matrix resulting in tissue fibrosis (See Border and Noble, *N. Eng. J. Med.* 331:1286–1292(1994)). Another possible explanation for persistent TGFα overexpression is the presence of a biologically complex interconnection between TGFβ and the renin-angiotensin system (RAS) in the kidney as part of an emergency system that responds to the threat of tissue injury as discussed further herein.

Renin is an aspartyl proteinase synthesized by juxtaglomerular kidney cells and mesangial cells in humans and rats. (Chansel et al., *Am. J. Physiol.* 252:F32–F38 (1987) and Dzau and Kreisberg, *J. Cardiovasc. Pharmacol.* 8(Suppl 10):S6–S10(1986)). Renin plays a key role in the regulation of blood pressure and salt balance. Its major source in humans is the kidney where it is initially produced as preprorenin. Signal peptide processing and glycosylation are followed by secretion of prorenin and its enzymatically active form, mature renin. The active enzyme triggers a proteolytic cascade by cleaving angiotensinogen to generate angiotensin I, which is in turn converted to the vasoactive hormone angiotensin II by angiotensin converting enzyme ("ACE").

The sequence of the human renin gene is known (GenBank entry M2690). Recombinant human renin has been synthesized and expressed in various expression systems (Sielecki et al., *Science* 243:1346–1351(1988), Mathews et al., *Protein Expression and Purification* 7:81–91 (1996)). Inhibitors of renin's enzymatic site are known (Rahuel et al., *J. Struct. Biol.* 107:227–236 (1991); Badasso et al., *J. Mol. Biol.* 223:447–453 (1992); and Dhanaraj et al., *Nature* 357:466–472 (1992)) including an orally active renin inhibitor in primates, Ro 42-5892 (Fischli et al., *Hypertension* 18:22–31(1991)). Renin-binding proteins and a cell surface renin receptor on human mesangial cells have been identified (Campbell and Valentijn, *J. Hypertens.* 12:879–890 (1994), Nguyen et al., *Kidney Internat.* 50:1897–1903 (1996) and Sealey et al., *Amer. J. Hyper.* 9:491–502 (1996)).

The renin-angiotensin system (RAS) is a prototypical systemic endocrine network whose actions in the kidney and adrenal glands regulate blood pressure, intravascular volume and electrolyte balance. In contrast, TGFβ is considered to be a prototypical cytokine, a peptide signaling molecule whose multiple actions on cells are mediated in a local or paracrine manner. Recent data however, indicate that there is an intact RAS in many tissues whose actions are entirely paracrine and TGFα has wide-ranging systemic (endocrine) effects. Moreover, RAS and TGFε act at various points to regulate the actions of one another.

In a systemic response to an injury such as a wound, the RAS rapidly generates AII that acts by vasoconstriction to maintain blood pressure and later stimulates the secretion of aldosterone, resulting in an increase in intravascular volume. In the wound, TGFβ is rapidly released by degranulating platelets and causes a number of effects including: 1) auto-induction of the production of TGFβ by local cells to amplify biological effects; 2) chemoattraction of monocyte/macrophages that debride and sterilize the wound and fibroblasts that begin synthesis of ECM; 3) causing deposition of new ECM by simultaneously stimulating the synthesis of new ECM, inhibiting the proteases that degrade matrix and modulating the numbers of integrin receptors to facilitate cell adhesion to the newly assembled matrix; 4) suppressing the proinflammatory effects of interleukin-1 and tumor necrosis factor; 5) regulating the action of platelet derived growth factor and fibroblast growth factor so that cell proliferation and angiogenesis are coordinated with matrix deposition; and 6) terminating the process when repair is complete and the wound is closed (Border and Noble, Scientific Amer. Sci. & Med. 2:68–77 (1995)).

Interactions between RAS and TGFβ occur at both the systemic and molecular level. It has been shown that TGFβ's action in causing ECM deposition in a healing wound is the same action that makes TGFβ a powerful fibrogenic cytokine. (Border and Noble, New Engl. J. Med. 331:1286–1292(1994); and Border and Ruoslahti, J. Clin. Invest. 90:107 (1992). Indeed, it is the failure to terminate the production of TGFβ that distinguishes normal tissue repair from fibrotic disease. RAS and TGFβ co-regulate each other's expression. Thus, both systems may remain active long after an emergency response has been terminated, which can lead to progressive fibrosis. The kidney is particularly susceptible to overexpression of TGFβ. The interrelationship of RAS and TGFβ may explain the susceptibility of the kidney to TGFβ overexpression and why pharmacologic suppression of RAS or inhibition of TGFβ are both therapeutic in fibrotic diseases of the kidney. (Noble and Border, Sem. Nephrol., supra and Border and Noble, Kidney Int. 51:1388–1396 (1997)).

Activation of RAS and generation of angiotensin II (AII) are known to play a role in the pathogenesis of hypertension and renal and cardiac fibrosis. TGFβ has been shown to be a powerful fibrogenic cytokine, acting simultaneously to stimulate the synthesis of ECM, inhibit the action of proteases that degrade ECM and increasing the expression of cell surface integrins that interact with matrix components. Through these effects, TGFβ rapidly causes the deposition of excess ECM. AII infusion strongly stimulates the production and activation of TGFβ in the kidney. (Kagami et al., J. Clin. Invest. 93:2431–2437 (1994)). Angiotensin II also upregulates TGFβ production and increases activation when added to cultured vascular smooth muscle cells (Gibbons et al, J. Clin. Invest. 90:456–461 (1992)) and this increase is independent of pressure (Kagami et al., supra). AII also upregulates TGFβ receptors, even in the presence of exogenously added TGFβ which normally down-regulates its own receptors, leading to enhanced TGFβ signalling and enhanced fibronectin production (Kanai et al., J. Am. Soc. Nephrol. 8:518A (1997)). Blockade of AII reduces TGFβ overexpression in kidney and heart, and it is thought that TGFβ mediates renal and cardiac fibrosis associated with activation of RAS (Noble and Border, Sem. Nephrol. 17(5):455–466 (1997)), Peters et al., Kidney International 54 (1998)). Blockade of AII using inhibitors of ACE slow the progression of renal fibrotic disease (see, e.g., Anderson et al., J. Clin. Invest. 76:612–619 (1985) and Noble and Border, Sem. Nephrol. 17(5):455–466 (1997)). What is not clear is whether angiotensin blockade reduces fibrosis solely through controlling glomerular hypertension and thereby glomerular injury, or whether pressure-independent as well as pressure-dependent mechanisms are operating. While ACE inhibitors and AII receptor antagonists have been shown to slow the progress of fibrotic diseases, they do not halt disease and TGFβ levels remain somewhat elevated. (Peters et al., supra).

Thus, RAS and TGFβ can be viewed as powerful effector molecules that interact to preserve systemic and tissue homeostasis. The response to an emergency such as tissue injury is that RAS and TGFβ become activated. Continued activation may result in chronic hypertension and progressive tissue fibrosis leading to organ failure. Because of the interplay between the RAS and TGFβ, and the effects of this interplay on tissue homeostasis, blockade of the RAS may be suboptimal to prevent or treat progressive fibrotic diseases such as diabetic nephropathy.

Components of the renin-angiotensin system act to further stimulate production of TGFβ and plasminogen activator inhibitor leading to rapid ECM accumulation. The protective effect of inhibition of the renin-angiotensin system in experimental and human kidney diseases correlates with the suppression of TGFβ production. (Noble and Border, Sem. Nephrol., supra; and Peters et al., supra).

The renin molecule has been shown to enzymatically cleave angiotensinogen into angiotensin I. The angiotensin I is then converted by Angiotensin Converting Enzyme ("ACE") to Angiotensin II which acts as an active metabolite and induces TGFβ production. Angiotensin II is an important modulator of systemic blood pressure. It has been thought that if you decrease hypertension by blocking AII's vasoconstrictor effects fibrotic disease is reduced.

In the glomerular endothelium, activation of RAS and TGFβ have been shown to play a role in the pathogenesis of glomerulonephritis and hypertensive injury. Volume (water) depletion and restriction of potassium have been shown to stimulate both production of renin and TGFβ in the juxtaglomerular apparatus (JGA) of the kidney (Horikoshi et al., J. Clin. Invest. 88:2117–2122 (1992) and Ray et al., Kidney Int. 44:1006–1013 (1993)). Angiotensin blockade has also been shown to increase the production of renin. TGFβ has been shown to stimulate the release of renin from kidney cortical slices and cultured JG cells (Antonipillai et al., Am. J. Physiol. 265:F537–F541 (1993); Ray et al., Contrib. Nephrol. 118:238–248 (1996) and Veniant et al., J. Clin. Invest. 98:1996–19970 (1996)), suggesting that renin and TGFβ are coregulated. Other interactions between RAS and TGFβ include that AII induces the production of TGFβ in cultured cells and in vivo (Kagami et al., supra) and AII regulates expression of TGFβ receptors (Kanai et al., 1977, supra). It is thus likely that the fibrogenic effects that have been attributed to AII are actually mediated by TGF.

Another interplay between RAS and TGFβ is with the production of aldosterone. Aldosterone overproduction has been linked to hypertension and glomerulosclerosis. AII stimulates the production and release of aldosterone from the adrenal gland. In contrast, TGFβ suppresses aldosterone production and blocks the ability of AII to stimulate aldosterone by reducing the number of AII receptors expressed in the adrenal (Gupta et al., Endocrinol. 131:631–636 (1992)), and blocks the effects of aldosterone on sodium reabsorption in cultured renal collecting duct cells (Husted et al., Am. J. Physiol. Renal, Fluid Electrolyte Physiol. 267:F767–F775 (1994)). Aldosterone may have fibrogenic effects independent of AII, and may upregulate TGFβ expression. The mechanism of aldosterone's pathological effects is unknown but might be due to stimulation of TGFβ production in the kidney (Greene et al., J. Clin. Invest. 98:1063–1068 (1996)).

Prorenin or renin may have AII-independent actions to increase fibrotic disease. Prorenin overexpressing rats were found to be normotensive but to develop severe glomerulosclerosis (Veniant et al., J. Clin. Invest. 98:1996–1970 (1996)).

Human recombinant renin added to human mesangial cells induces marked upregulation of production of plasminogen activator inhibitors (e.g. PAI-1 and PAI-2) which block the generation of plasmin, a fibrinolytic enzyme important in the dissolution of clots after wounding generated from plasminogen by two enzymes called plasminogen activators, urokinase (u-PA) and tissue plasminogen activator (t-PA). PAI-1 and 2 regulate U-PA and t-PA in turn. Plasmin appears to be a key mediator of extracellular matrix degradation, carrying out at least three functions important to extracellular matrix degradation. Plasmin directly degrades proteoglycan components of extracellular matrix, proteolytically activates metalloproteinases (MMPs) that, in turn, degrade collagens and other matrix proteins, and enzymatically inactivates tissue inhibitors of MMPs (TIMPs), releasing MMPs from inhibition of TIMPs, allowing them to proteolytically digest matrix proteins. (Baricos et al., Kidney Int'l. 47:1039–1047(1995); Baricos et al., J. Amer. Soc. Nephrol. 10:790–795 (1999)). The net generation of active plasmin from the inactive precursor plasminogen results from a balance of the plasminogen activators and PAI-1 and 2, and other factors. PAI-1 binds to vitronectin. (Lawrence et al., J. Biol. Chem. 272:7676–7680 (1997)). Mutant PAI-1 molecules have been developed that have enhanced properties for PAI-1 binding to vitronectin molecules, but do not inhibit either t-PA or u-PA activity, resulting in an increase in the amount of the active form of plasmin. (See, WO 97/39028, Lawrence et al.). PAI-1 is increased in response to added TGFβ (Tomooka et al., Kidney Int. 42:1462–1469 (1992)).

It has been suggested that TGFβ enhances release of renin from storage granules in the juxtaglomerular apparatus of the kidney (Antonipillai et al., Am. J. Physiol. 265:F537–F541 (1993) and Ray et al., Contrib. Nephrol. 118:238–248 (1996)).

Thus, the interactions of RAS and TGFβ production form a complex system which impacts fibrotic ECM accumulation and the incidence of fibrotic disease. Various RAS components such as aldosterone, prorenin and renin may be connected with TGFβ production and fibrotic ECM accumulation. Any successful therapeutic regime must take into account these complex relationships to optimize inhibition of TGFβ to prevent and/or reduce ECM accumulation.

The multiple pathways resulting in TGFβ overexpression and fibrosis proposed from in vitro studies are depicted in FIG. 1. (See, Kagami et al., J. Clin. Invest. 93:2431–2437 (1994); Gibbons et al., J. Clin. Invest. 90:456–461 (1992); Abboud, Kidney Int. 41:581–583 (1992); Ruiz-Ortega et al., J. Am. Soc. Nephrol. 5:683 (1994) abstract; Kim et al., J. Biol. Chem. 267:13702–13707 (1992); Ohno et al., J. Clin. Invest. 95:1363–1369 (1995); Riser et al, J. Clin. Invest. 90:1932–1943 (1992); Riser et al., J. Am. Soc. Nephrol. 4:663 (1993); Ziyadeh et al., J. Clin. Invest. 93:536–542 (1994); Rocco et al., Kidney Int. 41:107–114 (1992); Flaumenhaft et al., Advan. Pharmacol. 24:51–76 (1993); Lopez-Armanda et al., J. Am. Soc. Nepbrol. 5:812 (1994) abstract; Sahai et al., J. Am. Soc. Nephrol. 6:910 (1995); Remuzzi et al., Kidney Int. 1:2–15 (1997); and Remuzzi et al., J. Am. Soc. Nephrol. 9:1321–1332 (1998)). This diagram shows that a large number of factors implicated in kidney injury are believed to increase the production of TGFβ.

In fibrotic diseases overproduction of TGFβ results in excess accumulation of extracellular matrix which leads to tissue fibrosis and eventually organ failure. Accumulation of mesangial matrix is a histological indication of progressive glomerular diseases that lead to glomerulosclerosis and end-stage kidney disease (Klahr et al., N. Engl. J. Med. 318:1657–1666 (1988); Kashgarian and Sterzel, Kidney Int. 41:524–529 (1992)). Rats injected with antithymocyte serum are an accepted model of human glomerulonephritis and this model has demonstrated that overproduction of glomerular TGFβ can underlie the development of glomerulosclerosis (Okuda et al., J. Clin. Invest. 86:453–462 (1990); Border et al., Nature (Lond.) 346:371–374 (1990); Kagami et al., Lab. Invest. 69:68–76 (1993); and Isaka et al., J. Clin. Invest. 92:2597–2602 (1993)). Using cultured rat mesangial cells where the effects of Angiotensin II on glomerular pressure are not a factor, Angiotensin II has been shown to induce TGFβ production and secretion by mesangial cells, and this in turn has been shown to stimulate extracellular matrix production and deposition (Kagami et al., J. Clin. Invest. 93:2431–2437 (1994)). Increases in PAI-1 levels result in decreased degradation of extracellular matrix (Baricos et al., Kidney Int. 47:1039–1047 (1995)). Increases in TGFβ result in increased PAI-1 levels (Tomooka et al., Kidney Int. 42:1462–1469 (1992)). It has been demonstrated that decreasing TGFβ overexpression in a rat model of glomerulonephritis by in vivo injection of neutralizing antibodies to TGFβ, reduces TGFβ overexpression (Border et al., Nature 346:371–374 (1990)), and reduces PAI-1 deposition into the pathological matrix (Tomooka et al., Kidney Int. 42:1462–1469 (1992)). Therefore, decreases in TGFβ levels should result in decreased PAI-1 levels and increased degradation of extracellular matrix to ameliorate organ impairment and fibrotic disease. However, patients present with fibrotic disease that is well advanced in terms of build-up of extra-cellular matrix (ECM). This is because abnormal organ function is undetectable until ECM accumulation is very advanced. For example, in the kidney, standard diagnostic tests do not provide an abnormal reading until about fifty percent of organ function has been lost.

The treatment of conditions associated with excess accumulation of ECM has also focused on decreasing stimuli to disease such as to lower blood pressure or, in the case of diabetic nephropathy to reduce plasma glucose levels. For example, current therapies for treating fibrotic disease in the kidney are limited to AII blockade using ACE inhibitors such as Enalapril or AII receptor antagonists such as Losartan. In addition, patients are encouraged to follow low protein diets since this regimen has some therapeutic value (Rosenberg et al., J. Clin. Invest. 85:1144–1149(1992)). These therapies, at best, prolong organ function by only 1–2 years. This may be because of the multiple pathways that result in TGFβ overexpression or enhanced activity. Moreover, it is likely that current therapeutic strategies to reduce TGFβ overproduction may lead to upregulation of other pathways resulting in continued TGFβ overproduction. For example, when the action of AII is blocked, renin is upregulated which itself increases TGFβ production (see co-pending U.S. patent application, U.S. Ser. No. 09/005,255, incorporated in its entirety herein). More recently, treatments aimed to halt the overproduction of TGFβ have been proposed (Border and Noble, Kidney Internatl. 54 (1998); and Peters et al., Kidney Internatl. 54 (1998)).

Therefore, the most promising therapeutic methods will need to increase ECM degradation to restore organ function as well as decrease TGFβ overproduction and/or activity. Enhanced degradation of excess accumulated ECM can be used to optimize overall reduction in levels of accumulated ECM to restore function to tissues and organs. Proteases that are able to degrade ECM are known. For example, the serine protease plasmin degrades ECM proteins and activates prometalloproteinases, in addition to degrading fibrin (Baricos et al., supra). One goal of therapeutic intervention to increase ECM degradation for treating fibrosis could be increasing plasmin in the region of excess ECM deposition.

There is a need for improved therapies to normalize TGFβ production, that take into account the multiple pathways that stimulate TGFβ production, to prevent or reduce excess accumulation of ECM, to restore function to tissues and organs in which excess ECM has accumulated and/or to reduce scar formation at a wound site.

SUMMARY OF THE INVENTION

Accordingly, the present invention provides methods for preventing or reducing the excess accumulation of extracellular matrix (ECM) associated with fibrotic conditions by inhibiting TGFβ, using a combination of agents that inhibit TGFβ, or by using a combination of agents to inhibit TGFβ and agents that cause the enhanced degradation of excess accumulated ECM.

The methods of the invention contemplate the use of agents that directly or indirectly inhibit TGFβ including direct inhibitors of TGFβ activity such as anti-TGFβ antibodies, proteoglycans such as decorin and ligands for TGFβ receptors, and/or indirect TGFβ inhibitors including aldosterone, inhibitors of aldosterone, inhibitors of angiotensin II, renin inhibitors, ACE inhibitors and AII receptor antagonists which act to decrease TGF production.

The methods of the invention also contemplate the use of agents that result in the enhanced degradation of excess accumulated matrix including proteases such as serine proteases including plasmin, metalloproteases, or protease combinations, and agents such as tPA, and PAI-1 mutants that increase the production and/or the activity of proteases such as plasmin.

The agents for use in the methods of the invention may be administered as inhibitory compounds in pharmaceutical formulations or as nucleic acid encoding the inhibitors delivered to suitable host cells. The nucleic acid may be directly introduced into a cell in vivo, for example into muscle tissue, or may be first introduced into a cell ex vivo to obtain a cell expressing the inhibitory agent or agents, and the cell then transplanted or grafted into a subject to inhibit or reduce excess accumulation of extracellular matrix.

The invention includes compositions for preventing or reducing the excess accumulation of ECM containing a combination of agents for inhibiting TGFβ or a combination of agents for inhibiting TGFβ and for degrading ECM.

DETAILED DESCRIPTION OF THE INVENTION

Figure 1:
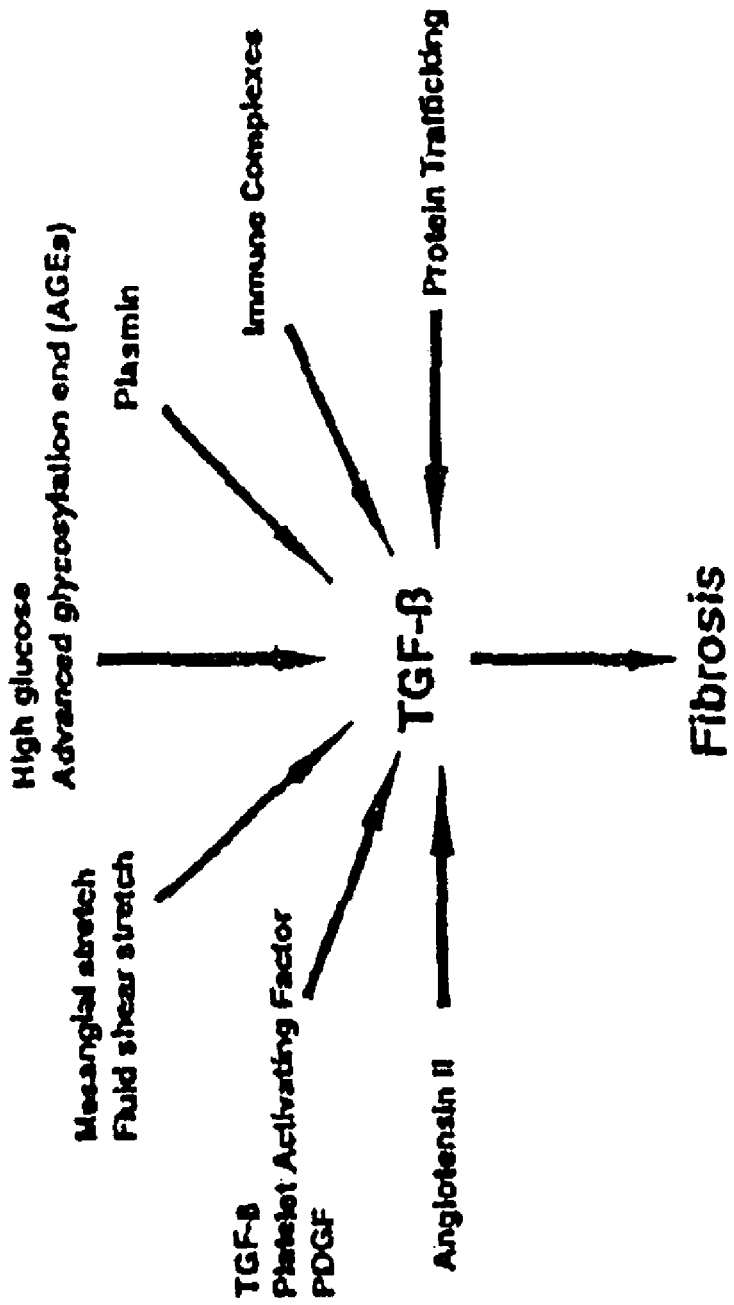
FIG. 1 is a diagram depicting various pathways resulting in increased TGFβ production.

The present invention is based on the discovery that a combination of strategies may be warranted to prevent or treat conditions associated with the excess accumulation of extracellular matrix in tissues or organs, including fibrotic diseases and scarring resulting from TGFβ overproduction and/or activity. As previously reported, TGFβ overproduction may result from multiple pathways and require that more than one pathway be inhibited to achieve any clinically significant reduction in excess accumulation of extracellular matrix and amelioration of disease. For example, as disclosed in co-pending U.S. patent application, U.S. Ser. No. 09/005,255, incorporated in its entirety herein, renin stimulates TGFβ production in cells capable of producing TGFβ, in an angiotensin-II and blood pressure-independent manner.

Optimal therapy of disorders associated with excess accumulation of ECM which causes organ impairment and ultimately failure, must take into account the multiple pathways of TGFβ production to effectively combat overproduction of TGFβ. Without such multifactorial stagy, inhibition of one pathway of TGFβ production may be insufficient to block excess accumulation of extracellular matrix and can even result in an increase in the levels of TGFβ production by stimulation of one of the alternative pathways for its production.

While it is now known that multiple stimuli result in TGFβ overexpression and resulting excess accumulation of ECM, therapeutic strategies directly inhibiting TGFβ, such as the use of anti-TGFβ antibodies or TGFβ receptor antagonists, are being explored. However because TGFβ has many beneficial actions such as immunosuppressive and immunomodulatory effects, as well as inhibition of epithelial cell growth which retards carcinogenesis (Markowitz, *Science* 268:1336–1338 (1995) and suppression of atherogenesis (Grainger et al., *Nature Med.* 1:74–79 (1995), these therapies may have unacceptable side-effects if administered at doses high enough to successfully stem fibrotic conditions. This has been shown in the TGFβ 1 null (knockout) mice which die of overwhelming inflammation at about 6 weeks of age (Letterio et al., *Science* 264:1936–1938 (1994); Kulkami et al, *Proc. Natl. Acad. Sci. USA* 90:770–774 (1993) and Shull et al., *Nature* 359:693–699

(1992)), indicating that TGFβ1 has significant beneficial roles in immune function. Multiple agents, inhibiting TGFβ directly, and/or inhibiting the disease specific stimuli underlying TGFβ overexpression and/or activity, for example high glucose resulting from diabetes, may be required to adequately reduce TGFβ-associated excess accumulation of ECM, without causing harmful side-effects. Accordingly, it is a goal of the methods of the present invention to accomplish normalization of TGF production without harmful side effects and to prevent or reduce excess accumulation of ECM and ensuing fibrotic conditions.

In addition, degradation of accumulated ECM may be needed to restore tissue or organ function that has been compromised by the presence of the excess accumulated ECM. Prevention or degradation of excess accumulated ECM can also prevent or reduce scar formation at the site of a wound.

The methods of the invention include using multiple agents to reduce the overproduction and/or activity of TGFβ and/or to block alternative pathways of TGFβ production to prevent or reduce excess accumulation of ECM. The methods of the invention further include the use of a combination of agents to reduce TGFβ overproduction and/or activity in combination with agents to enhance the degradation of excess, accumulated ECM. The methods are useful to prevent or reduce excess accumulation of extracellular matrix to ameliorate fibrotic conditions, and to restore or maintain normal tissue or organ function or skin appearance.

As used herein "excess accumulation of extracellular matrix" means the deposition of extracellular matrix components including, collagen, laminin, fibronectin and proteoglycans in tissue to an extent that results in impairment of tissue or organ function and ultimately, organ failure as a result of fibrotic disease. In addition, "excess accumulation of extracellular matrix" means the deposition of extracellular matrix components in the process commonly referred to as "scarring" or "scar formation," e.g. at a wound site. "Reducing the excess accumulation of extracellular matrix" means preventing excess accumulation of extracellular matrix, e.g. in tissue, organs or at a wound site, preventing further deposition of extracellular matrix and/or decreasing the amount of excess accumulated matrix already present, to maintain or restore tissue or organ function or appearance.

A variety of conditions are characterized by excess accumulation of extracellular matrix (collagen, fibronectin and other matrix components). Such conditions include, for example, but are not limited to, glomerulonephritis, adult or acute respiratory distress syndrome (ARDS), diabetes-associated pathologies such as diabetic kidney disease, fibrotic diseases of the liver, lung and post infarction cardiac fibrosis. Also included are fibrocystic diseases such as fibrosclerosis and fibrotic cancers such as cancers of the breast, uterus, pancreas or colon, and including fibroids, fibroma, fibroadenomas and fibrosarcomas.

There are also a number of medical conditions associated with an excess accumulation of extracellular matrix involving increased collagen, fibronectin and other matrix components. Such conditions include, for example, but are not limited to, post myocardial infarction, left ventricular hypertrophy, pulmonary fibrosis, liver cirrhosis, veno-occlusive disease, post-spinal cord injury, post-retinal and glaucoma surgery, post-angioplasty restenosis and renal interstitial fibrosis, arteriovenous graft failure, excessive scarring such as keloid scars and scars resulting from injury, burns or surgery.

As discussed, supra it is known that TGFβ is indicated in the causation of fibrotic conditions. During normal tissue repair, TGFβ production is increased to stimulate the process of repair. When repair is complete, TGFβ production is reduced. If not reduced following normal tissue repair, the increased TGFβ overproduction can result in the development of excess extracellular matrix accumulation and fibrotic conditions. Thus, repeated tissue injury or a defect in TGFβ regulation leading to sustained TGF production results in excess accumulation of extracellular matrix.

As used herein "inhibition of TGFβ" includes inhibition of TGFβ activity, for example in causing excess deposition of ECM, as well as inhibition of TGFβ production resulting in overproduction and excess accumulation of ECM, regardless of the mechanism of TGFβ activity or overproduction. This inhibition can be caused directly, e.g. by binding to TGFβ or its receptors, for example by anti-TGFβ antibodies or TGFβ receptor antagonists, or can be caused indirectly, for example by inhibiting a pathway that results in TGFβ production, such as the renin pathway. Inhibition causes a reduction in the ECM producing activity of TGFβ regardless of the exact mechanism of inhibition.

As used herein a "TGFβ inhibitory agent" is an agent that directly or indirectly inhibits TGFβ binding to its receptors, such as a TGFβ-specific inhibitory agent, or an agent that blocks an alternative pathway of TGFβ production. The agent causes a reduction in the ECM producing activity of TGFβ regardless of the mechanism of its action. The agent can be nucleic acid encoding the TGFβ inhibitory agent such as a cDNA, genomic DNA, or an RNA or DNA encoding TGFβ inhibitory activity such as a TGFβ antisense RNA or DNA.

As used herein, a "TGFβ-specific inhibitory agent" means an agent containing TGFβ inhibiting activity, including agents that bind directly to TGFβ such as anti-TGFβ antibodies, or are a ligand for TGFβ which prevents it from binding to its receptors. A TGFβ-specific inhibiting agent also includes a nucleic acid encoding a particular TGFβ-specific inhibitory agent such as a cDNA, genomic DNA or an RNA or DNA encoding TGFβ-specific inhibitory activity such as a TGFβ antisense RNA or DNA.

Agents that bind directly to TGFβ are known and include anti-TGFβ antibodies such as anti-TGFβ1 antibodies (Genzyme, Cambridge, Mass.) and antibodies which bind both TGFβ1 and TGFβ2 (Dasch et al., U.S. Pat. No. 5,571,714), proteoglycans such as decorin, biglycan and fibromodulin, and the nucleic acids encoding such agents.

Antibodies to inhibit TGFβ, renin or other molecules, for use in the present invention, can be prepared according to methods well established in the art, for example by immunization of suitable host animals with the selected antigen, e.g. TGFβ. For descriptions of techniques for obtaining monoclonal antibodies see, e.g. the hybridoma technique of Kohler and Milstein (*Nature* 256:495–497 (1975)), the human B-cell hybridoma technique (Kosbor et al., *Immunol. Today* 4:72 (1983); Cole et al., *Proc. Nat'l. Acad. Sci. USA,* 80:2026–2030 (1983)) and the EBV-hybridoma technique (Cole et al., *Monoclonal antibodies and Cancer Therapy*, Alan R. Liss, Inc., pp. 77096 (1985)). Such antibodies may be of any immunoglobulin class including IgG, IgM, IgE, IgA, IgD and any subclass thereof. The hybridoma producing the monoclonal antibody may be cultivated in vitro or in vivo. Suitable host animals include, but are not limited to, rabbits, mice, rats, and goats. Various adjuvants may be used to increase the immunological response to the host animal, depending on the host species, including, but not limited to, Freund's (complete and incomplete), mineral gels such as aluminum hydroxide, surface active substances such as pluronic polyols, polyanions, peptides, oil emulsions, keyhole limpit, hemocyanin, dinitrophenol and potentially useful human adjuvants such as BCG (Bacille Calmette-Guerin) and Cornebacterium parvum. Antibodies as used herein includes non-human, chimeric (different species), humanized (see Borrebaeck, Antibody Engineering: A Practical Guide, W. H. Freeman and Co., New York, 1991), human and single-chain antibodies, as well as antibody fragments including but not limited to the F(ab')$_2$ fragments that can be produced by pepsin digestion of antibody molecules and Fab fragments that can be generated by reducing disulfide bridges of the F(ab')$_2$ fragments. Alternatively, Fab expression libraries may be constructed (Science 246:1275–1281 (1989)) to permit the rapid and easy identification of monoclonal Fab fragments having the desired specificity.

An indirect TGFβ inhibitor would inhibit the synthesis or secretion of TGFβ or sequester it away from its target cells. Such inhibitors include, but are not limited to, inhibitors of Angiotensin Converting Enzyme ("ACE"), antagonists of the AII receptor such as Losartan™ and Cozar™ (Merck), and aldosterone inhibitors such as Spironolactone™ (Sigma Chemical Co., St. Louis, Mo., Product # S 3378) that would otherwise result in increased TGFβ production.

Also included within the scope of TGFβ inhibitors of the invention are nucleic acids that include antisense oligonucleotides that block the expression of specific genes within cells by binding a complementary messenger RNA (mRNA) and preventing its translation (See review by Wagner, *Nature* 372:332–335 (1994); and Crooke and Lebleu, *Antisense Research and Applications*, CRC Press, Boca Raton (1993)). Gene inhibition may be measured by determining the degradation of the target RNA. Antisense DNA and RNA can be prepared by methods known in the art for synthesis of RNA including chemical synthesis such as solid phase phosphoramidite chemical synthesis or in vitro and in vivo transcription of DNA sequences encoding the antisense RNA molecule. The DNA sequences may be incorporated into vectors with RNA polymerase promoters such as the T7 or SP6 polymerase promoters. Alternatively, antisense cDNA constructs that synthesize antisense RNA constitutively or inducibly can be introduced into cell lines. The potency of antisense oligonucleotides for inhibiting TGFβ may be enhanced using various methods including 1) addition of polylysine (Leonetti et al., *Bioconj. Biochem.* 1:149–153 (1990)); 2) encapsulation into antibody targeted liposomes (Leonetti et al., *Proc. Natl. Acad. Sci. USA* 87:2448–2451 (1990) and Zelphati et al., *Antisense Research and Development* 3:323–338 (1993)); 3) nanoparticles (Rajaonarivony et al., *J. Pharmaceutical Sciences* 82:912–917 (1993) and Haensler and Szoka, *Bioconj. Chem.* 4:372–379 (1993)), 4) the use of cationic acid liposomes (Felgner et al., *Proc. Natl. Acad. Sci. USA* 84:7413–7417 (1987); Capaccioli et al., *Biochem. Biophys. Res. Commun.* 197:818–825 (1993); Boutorine and Kostina, Biochimie 75:35–41 (1993); Zhu et al., *Science* 261:209–211 (1993); Bennett et al., *Molec. Pharmac.* 41:1023–1033 (1992) and Wagner, *Science* 280:1510–1513 (1993)); and 5) Sendai virus derived liposomes (Compagnon et al., *Exper. Cell Res.* 200:333–338 (1992) and Morishita et al., *Proc. Natl. Acad. Sci. USA* 90:8474–8478 (1993)), to deliver the oligonucleotides into cells. Recent techniques for enhancing delivery include the conjugation of the antisense oligonucleotides to a fusogenic peptide, e.g. derived from an influenza hemagglutinin envelop protein (Bongartz et al., *Nucleic Acids Res.* 22(22):4681–4688 (1994)).

Additional suitable TGFβ inhibitory agents can be readily obtained using methods known in the art to screen candidate agent molecules for binding to TGFβ, such as assays for detecting the ability of a candidate agent to block binding of radiolabeled human TGFβ to cells such as human mesangial cells. Alternatively, candidate compounds may be tested for the ability to inhibit TGFβ production by mesangial cells using an enzyme-linked immunosorbent assay (ELISA), for example using the R & D Systems (Minneapolis, Minn.) TGFβ ELISA assay kit (Cat. No. DB 100) (for methods see, e.g. Uotila et al., *J. Immunol. Methods* 42:11 (1981)).

Suitable TGFβ-specific inhibitory agents can also be developed by known drug design methods, e.g. using structural analysis of the TGFβ molecule employing methods established in the art, for example, using X-ray crystallography to analyze the structure of the complex formed by TGFβ and one of its known inhibitors (see, e.g. Sielecki et al., supra; Rahuel et al., supra, Badasso et al., supra and Dhanaraj et al., supra.), and/or by modifying known TGFβ antagonists i.e. "lead compounds," to obtain more potent inhibitors and compounds for different modes of administration (i.e. oral vs. intravenous) (see, e.g. Wexler et al., *Amer. J. Hyper.* 5:209S–220S (1992)-development of AII receptor antagonists from Losartan™). For such procedures large quantities of TGFβ can be generated using recombinant technology or purchased commercially (R & D Systems).

In addition to TGFβ inhibitory agents, agents that result in the degradation of ECM are contemplated for use in the invention. Such agents include serine proteases such as plasmin and metalloproteinases, and protease combinations such as Wobenzym (Mucos Pharma, Geretsried, Germany). In addition, the present inventors have discovered that agents such as tPA can be used to increase the amount of active proteases in vivo to increase degradation of ECM accumulated in organs and tissues. Tissue plasmin activator (tPA, Activase, Genentech, S. San Francisco, Calif.) has been shown to dissolve clots associated with myocardial infarction and stroke. The present inventors theorized that tPA might be helpful in increasing plasmin to reduce accumulated ECM. Shown herein is the use of recombinant tPA (rtPA) to increase the generation of plasmin in vivo to degrade ECM (Example V, infra).

In addition, new proteases or agonists of protease production and/or activity may be discovered or developed using rational drug design and used to degrade ECM according to the methods of the present invention.

The present inventors have also discovered that PAI mutants, such as the PAI-1 mutants disclosed in WO 97/39028 by Lawrence et al., incorporated by reference in its entirety herein, may be used to increase the amount of active plasmin to enhance degradation of ECM accumulated in organs and tissues. These PAI-1 mutants fail to inhibit plasminogen activators, yet retain significant vitronectin binding affinity. Additional PAI-1 mutants for use in the methods of the invention may be obtained and tested for the ability to bind vitronectin while failing to inhibit plasminogen activators (Lawrence et al., *J. Biol. Chem.* 272:7676–7680 (1997)). PAI-1 binding to vitronectin may be determined either functionally (Lawrence et al., *J. Biol. Chem.* 265:20293–20301 (1990)) or in a vitronectin specific ELISA (Lawrence et al., *J. Biol. Chem.* 269:15223–15228 (1994)). The ability of PAI-1 to inhibit plasminogen activators may be evaluated using chromogenic assays as described by Sherman et al., *J. Biol. Chem.* 270:9301–9306 (1995)).

In the methods of the invention, the TGFβ inhibitory agents are administered concurrently or sequentially. For example, an anti-TGFβ antibody is administered with an anti-renin agent. The inhibitory agents will localize at sites of TGFβ overproduction, e.g. organs such as the kidneys. The inhibitory agents may be labelled, using using known radiolabelling methods to detect their localization in a subject after administration. The agents may also be conjugated to targeting molecules such as antibodies to ECM components to improve localization of the agents after administration to the sites of TGFβ overproduction and/or excess accumulation of ECM in a subject.

In another embodiment of the methods of the invention, TGFβ inhibitory agents are administered concurrently or sequentially with at least one agent that degrades accumulated ECM, for example, a serine protease such as plasmin. Alternatively, an agent that induces protease production, such as tPA, is administered to increase protease production at the site(s) of accumulated ECM. tPA binds fibrin (Rondeau et al., *Clinical Nephrol.* 33:55–60 (1990)) and thus will localize in fibrotic areas where the increased protease production is desired.

In one embodiment of the invention, at least one TGFβ-inhibitory agent is administered to a subject having existing excess accumulation of ECM in tissues or organs, or at high risk for such accumulation to reduce or prevent excess accumulation of ECM. For example, individuals at risk for developing fibrotic conditions, such as a person having or at high risk for diabetes, high blood pressure, autoimmune disease (e.g. lupus) and inflammatory diseases can be scanned using known medical procedures including tissue biopsies of kidney, lung or liver, to determine whether ECM has accumulated in these organs. If the agent is TGFβ-specific, it binds to circulating TGFβ or tissue TGFβ. If the agent indirectly inhibits TGFβ, for example an anti-renin agent, it reduces the amount of TGFβ produced. As a result of the administration of agents that directly or indirectly inhibits TGFβ, ECM that has accumulated at the time of diagnosis or treatment, as well as further accumulation of ECM is reduced. Moreover, in high risk individuals the methods of the invention for inhibiting TGFβ overproduction with multiple agents can result in prevention of excess accumulation of ECM and the development of fibrotic conditions.

In another embodiment of the methods of the invention, at least one TGFβ inhibitory agent is administered to a subject having an existing excess accumuation of ECM in tissues or organs together with at least one agent to degrade accumulated ECM. The ECM degradation is accomplished using a protease, or an agent that enhances production or the activity of ECM degrading agents such as proteases. As a result of the administration of these agents, excess matrix accumulated at the time of diagnosis or treatment, as well as further excess accumulation of ECM is reduced.

In addition to the use of molecules such as antibodies and purified compound such as decorin, nucleic acid encoding the TGFβ inhibitory agents and nucleic acid encoding the agent to directly or indirectly degrade accumulated ECM, are administered to the subject to permit the agents to be expressed and secreted, for inhibiting TGFβ and degrading accumulated ECM. The nucleic acid may be introduced into cells in the subject, for example using a suitable delivery vehicle such as an expression vector or encapsulation unit such as a liposome, or may be introduced directly through the skin, for example in a DNA vaccine.

Alternatively, the nucleic acids encoding the agents are introduced into a cell ex vivo and the cells expressing the nucleic acids are introduced into a subject, e.g. by implantation procedures, to deliver the agents in vivo. Multiple agents can be introduced into a delivery vehicle or in separate vehicles.

Gene Therapy Methods

Methods for obtaining nucleic acids encoding TGFβ inhibitory agents and ECM degrading agents are known in the art. Following is a general description of methods of using the nucleic acids in gene therapy to reduce excess accumulation of ECM.

In one embodiment of the invention, gene therapy is contemplated using nucleic acids encoding the TGFβ inhibitory agents and/or the ECM degradation agent, introduced into cells in a subject to suppress TGFβ overproduction and to degrade accumulated ECM. Gene transfer into cells of these nucleic acids is contemplated in the methods of the invention.

Nucleic Acids

Large amounts of the nucleic acid sequences encoding the TGFβ-inhibiting agents and/or the ECM degradation agents may be obtained using well-established procedures for molecular cloning and replication of the vector or plasmid carrying the sequences in a suitable host cell. DNA sequences encoding a specific agent can be assembled from cDNA fragments and oligonucleotide linkers, or from a series of oligonucleotides to provide a synthetic inhibitor agent gene and/or ECM degradation gene which can be expressed. Such sequences are preferably provided in an open reading frame uninterrupted by internal non-translated sequences of introns, which are typically present in eukaryotic genes. Genomic DNA containing the relevant sequences can also be used. Sequences of non-translated DNA may be present 5' to 3' from the open reading frame, where such sequences do not interfere with manipulation or expression of the coding regions. Either complete gene sequences or partial sequences encoding the desired agents are employed.

The nucleic acid sequences encoding the agents can also be produced in part or in total by chemical synthesis, e.g. by the phosphoramidite method described by Beaucage and Carruthers, *Tetra Letts.* 22:1859–1862 (1981) or the triester method (Matteucci et al., *J. Am. Chem. Soc.* 103:3185 (1981) and may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

Gene Transfer

For gene transfer, the key steps are 1) to select the mode of delivery, e.g. a proper vector for delivery of the inhibitor genes to the subject, 2) administer the nucleic acid to the subject; and 3) achieve appropriate expression of the transferred gene for satisfactory durations. Methods for gene transfer are known in the art. The methods described below are merely for purposes of illustration and are typical of those that can be used to practice the invention. However, other procedures may also be employed, as is understood in the art. Most of the techniques to construct delivery vehicles such as vectors and the like are widely practiced in the art, and most practitioners are familiar with the standard resource materials which describe specific conditions, reagents and procedures. The following paragraphs may serve as a guideline.

Techniques for nucleic acid manipulation are well known. (See, e.g. *Annual Rev. of Biochem.* 61:131–156 (1992)). Reagents useful in applying such techniques, such as restriction enzymes and the like, are widely known in the art and commerically available from a number of vendors.

The natural or synthetic nucleic acid coding for the inhibitors for expression in a subject may be incorporated into vectors capable of introduction into and replication in the subject. In general, nucleic acid encoding the selected inhibitor molecules and/or ECM degradation molecules are inserted using standard recombinant techniques into a vector containing appropriate transcription and translation control sequences, including initiation sequences operably linked to the gene sequence to result in expression of the recombinant genes in the recipient host cells. "Operably linked" means that the components are in a physical and functional relationship permitting them to function in their intended manner.

For example, a promoter is operably linked to a coding sequence if the promoter effects its transcription or expression.

Sequences encoding selected inhibitor and/or degradation genes will include at least a portion of the coding sequence sufficient to provide the TGFβ inhibitory or ECM degradation activity in the expressed molecule. For example, in the case of a renin inhibitor, a portion of the coding sequence that enables the inhibitor to bind to renin can be used. Methods for determining such portions or "domains" including binding domains of molecules, are known in the art (See, e.g., Linsley et al., *Proc. Natl. Acad. Sci. USA* 87:5031–5035 (1990)). It is possible that it may be necessary to block both the renin enzymatic site and the renin-cell binding domain in order to effectively prevent the stimulus to TGFβ overproduction by renin. In such case, renin antisense molecules can be prepared using standard methods to accomplish complete blockade.

The selected nucleic acid sequences are inserted into a single vector or separate vectors. More than one gene encoding a selected agent, or portion thereof containing the desired activity, may be inserted into a single vector or into separate vectors for introduction into the host cells. Alternatively, these sequences can be administered as naked nucleic acid sequences or as part of a complex with other molecules, e.g. liposomes.

A variety of expression vectors and gene transfer methods useful for obtaining expression of selected molecule in recipient cells are well known in the art, and can be constructed using standard ligation and restriction techniques (see, for example, Sambrook et, al., *Molecular Cloning: A Laboratory Manual*, Cold Spring Harbor Laboratory Press, 1989; Maniatis et al., *Molecular Cloning: A Laboratory Manual*, Cold Spring Harbor, N.Y. (1982), Kriegler, *Gene Transfer and Expression: A Laboratory Manual* (W.H. Freeman and Co., New York, N.Y. 1990) and Wu, *Methods in Enzymol*. (Academic Press, New York, N.Y. 1993), each of which is incorporated by reference herein). The choice of vector or method depends on several factors such as the particular molecule to be expressed.

Suitable vectors may be plasmid or viral vectors (Kaufman, in *Gene Expression Technology*, Goeddel (Ed.) (1991)) including baculoviruses, adenoviruses, poxviruses (Moss, *Current Opin. Biotech.* 3:518–522 (1993)), retrotransposon vectors (Cook et al., *Bio/Technology* 9:748–751(1991) and Chakraborty et al., *FASEB J.* 7:971–977 (1993)) adeno-associated viruses (AAV) (Yei et al., *Gene Therapy* 1:192–200 (1994) and Smith et al., *Nat. Genet.* 5:397–402 (1993)), herpes virus and retrovirus vectors (Price et al., *Proc. Natl. Acad. Sci. USA* 84:156–160 (1987); Naviaux and Verma, *Current Opinion in Biotechnol.* 3:540–547 (1992); Hodgson and Chakraborty, *Curr. Opin.*

*Thera. Patients* 3:223–235 (1993)) such as the MMLV based replication incompetent vector pMV-7 (Kirschmeier et al., *DNA* 7:219–225 (1988)), as well as human and yeast artificial chromosomes (HACs and YACs) (Huxley, *Gene Therapy* 1:7–12 (1994) and Huxley et al., *Bio/Technology* 12:586–590 (1994)). Plasmid expression vectors include plasmids including pBR322, pUC or Bluescript™ (Stratagene, San Diego, Calif.).

Vectors containing the nucleic acid encoding the selected agents are preferably recombinant expression vectors in which high levels of gene expression may occur, and which contain appropriate regulatory sequences for transcription and translation of the inserted nucleic acid sequence. Regulatory sequences refer to those sequences normally associated (e.g. within 50 kb) of the coding region of a locus which affect the expression of the gene (including transcription, translation, splicing, stability or the like, of the messenger RNA). A transcriptional regulatory region encompasses all the elements necessary for transcription, including the promoter sequence, enhancer sequence and transcription factor binding sites. Regulatory sequences also include, inter alia, splice sites and polyadenylation sites. An internal ribosome entry site (IRES) sequence may be placed between recombinant coding sequences to permit expression of more than one coding sequence with a single promoter.

Transcriptional control regions include: the SV40 early promoter region, the cytomegalovirus (CMV) promoter (human CMV IE94 promoter region (Boshart et al., *Cell* 41:521–530 (1985)); the promoter contained in the 3' long terminal repeat of Rous Sarcoma Virus or other retroviruses; the herpes thymidine kinase promoter, the regulatory sequences of the methallothionein gene; regions from the human IL-2 gene (Fujita et al., *Cell* 46:401–407(1986)); regions from the human IFN gene (Ciccarone et al., *J. Immunol.* 144:725–730 (1990); regions from the human IFN gene (Shoemaker et al., *Proc. Natl. Acad. Sci USA* 87:9650–9654 (1990); regions from the human IL-4 gene (Arai et al., *J. Immunol.* 142:274–282 (1989)); regions from the human lymphotoxin gene (Nedwin et al., *Nucl. Acids. Res.* 13:6361–6373 (1985)); regions from the human granulocyte-macrophage CSF gene (GM-CSF) (Miyatake et al., *EMBO J.* 4:2561–2568 (1985)) and others. When viral vectors are used, recombinant coding sequences may be positioned in the vector so that their expression is regulated by regulatory sequences such as promoters naturally residing in the viral vector.

Operational elements for obtaining expression may include leader sequences, termination codons and other sequences needed or preferred for the appropriate transcription and translation of the inserted nucleic acid sequences. Secretion signals may also be included whether from the native inhibitor or from other secreted polypeptides, which permit the molecule to enter cell membranes and attain a functional conformation. It will be understood by one skilled in the art that the correction type and combination of expression control elements depends on the recipient host cells chosen to express the molecules ex vivo. The expression vector should contain additional elements needed for the transfer and subsequent replication of the expression vector containing the inserted nucleic acid sequences in the host cells. Examples of such elements include, but are not limited to, origins of replication and selectable markers. Additionally, elements such as enhancer sequences, for example CMV enhancer sequences, may be used to increase the level of therapeutic gene expression (Armelor. *Proc. Natl. Acad. Sci. USA* 70:2702 (1973)).

The vector may contain at least one positive marker that enables the selection of cells carrying the inserted nucleic acids. The selectable molecule may be a gene which, upon introduction into the host cell, expresses a dominant phenotype permitting positive selection of cells carrying the gene ex vivo. Genes of this type are known in the art and include, for example, drug resistance genes such as hygromycin-B phosphotransferase (hph) which confers resistance to the antibiotic G418; the aminoglycoside phosphotransferase gene (neo or aph) from Tn5 which codes for resistance to the antibiotic G418; the dihydrofolate reductase (DHRF) gene; the adenosine deaminase gene (ADA) and the multi-drug resistance (MDR) gene.

Recombinant viral vectors are introduced into host cells using standard techniques. Infection techniques have been developed which use recombinant infectious virus particles for gene delivery into cells. Viral vectors used in this way include vectors derived from simian virus 40 (SV40; Karlsson et al., *Proc. Natl. Acad. Sci. USA* 82:158 (1985)); adenoviruses (Karlsson et al., *EMBO J.* 5:2377 (1986)); vaccinia virus (Moss et al., *Vaccine* 6:161 (1988)); and retroviruses (Coffin, in Weiss et al. (Eds.), RNA Tumor Viruses, 2nd Ed., Vol. 2, Cold Spring Laboratory, NY, pp. 17–71 (1985)).

Nonreplicating viral vectors can be produced in packaging cell lines which produce virus particles which are infectious but replication defective, rendering them useful vectors for introduction of nucleic acid into a cell lacking complementary genetic information enabling encapsidation (Mann et al., *Cell* 33:153 (1983); Miller and Buttimore, *Mol. Cell. Biol.* 6:2895 (PA317, ATCC CRL9078). Packaging cell lines which contain amphotrophic packaging genes able to transduce cells of human and other species origin are preferred.

Vectors containing the inserted inhibitor genes or coding sequences are introduced into host cell using standard methods of transfection including electroporation, liposomal preparations, Ca-PH-DNA gels, DEAE-dextran, nucleic acid particle "guns" and other suitable methods.

In additional to various vectors including viral vectors, other delivery systems may be used including, but not limited to, microinjection (DePamphilis et al., *BioTechnique* 6:662–680 (1988)); liposomal mediated transfection (Felgner et al., *Proc. Natl. Acad. Sci. USA* 84:7413–7417 (1987); Felgner and Holm, *Focus* 11:21–25 (1989) and Felgner et al., *Proc. West. Pharmacol. Soc.* 32:115–121 (1989)); use of naked or particle mediated DNA transfer and other methods known in the art. Recently, cationic liposomes have been used to enhance transfection (Felgner et al., *Nature* 349:351 (1991); Zhu et al., *Science* 261:209 (1993)).

Suitable host cells for gene transfer consist of vertebrate cells such as fibroblasts, keratinocytes, muscle cells, mesangial cells (see, Kitamura et al., *Kidney Int.* 48:1747–1757 (1995)), and any other suitable host cell including so-called universal host cells, i.e. cells obtained from a different donor than the recipient subject but genetically modified to inhibit rejection by the subject. Autologous cells are preferred, but heterologous cells are encompassed within the scope of the invention.

Expression of the selected TGFβ inhibitor genes after introduction into the host cells is confirmed using standard methods. For example, expression of TGFβ-specific inhibitory agents can be determined by assaying for the ability of the supernatant from transfected cells to inhibit the binding of radiolabeled TGFβ to human mesangial cells using Fluorescent Activated Cell Sorting (FACS) or ELISA. Expression from host cells of an agent that inhibits TGFβ indirectly, such as Losartan, can be confirmed by detecting a decrease in fibronectin production by mesangial cells exposed to supernatant from transfected cells, relative to controls. Expression of genes encoding ECM degrading agents can be determined using, for example, an in vitro system using mesangial cells cultured on a ECM substrate such as Matrigel™ (Collaborative Research, Inc., Bedford, Mass.) that contains the major components of the mesangial matrix, including laminin, type IV collagen, entactin and heparan sulfate proteoglycan, as described by Baricos et al., *Kidney Internatl.* 47:1039–1047 (1995)). The ECM substrate is radiolabeled and ECM degradation by the product of an expressed gene from transfected host cells is determined by measuring the release of radioactivity from the ECM into serum-free medium. These assay systems may also be employed to screen candidate TGFβ inhibiting and ECM degrading agents.

Administration of TGFβ Inhibitory Agents and Agents Degrading Accumulated ECM

Agents for inhibiting TGFβ and agents for degrading accumulated ECM are suspended in physiologically compatible pharmaceutical carriers, such as physiological saline, phosphate-buffered saline, or the like to form physiologically acceptable aqueous pharmaceutical compositions for administration to a subject. Parenteral vehicles include sodium chloride solution, Ringer's desctrose, dextrose and sodium chloride and lactated Ringer's solution. Other substances may be added a desired, such as antimicrobials.

The TGFβ inhibiting and ECM degrading agents may be administered together or apart, simultaneously or sequentially, to carry out the methods of the invention.

Modes of administration of the TGFβ inhibitory agents and ECM degrading agents are those known in the art for therapeutic agents and include parenteral, for example, intravenous (e.g. for antibody inhibitors or proteases), intraperitoneal, intramuscular, intradermal, and epidermal including subcutaneous and intradermal, oral (e.g. small molecule renin and TGFβ antagonists), or applied to mucosal surfaces, e.g. by intranasal administration using inhalation of aerosol suspensions, and by implanting to muscle or other tissue in the subject (e.g. for gene transfer of nucleic acid expressing renin and/or TGFα inhibitors). Suppositories and topical preparations are also contemplated.

The TGFβ inhibitory and ECM degrading agents are introduced in amounts sufficient to prevent or reduce excess accumulation of extracellular matrix in susceptible tissues and organs including, but not limited to, lung and kidney tissue. Before or after administration, if necessary to prevent or inhibit the subject's immune response to the vehicles carrying the inhibitors, immunosuppressant agents may be used. Alternatively, the vehicles carrying the TGFβ inhibitory and ECM degrading agents can be encapsulated.

The most effective mode of administration and dosage regimen for the TGFβ inhibitory and ECM degrading agents for use in the methods of the present invention depend on the extent of TGFβ overproduction, the severity of the accumulation of extracellular matrix and resulting impairment of tissue or organ function, the subject's health, previous medical history, age, weight, height, sex and response to treatment and the judgment of the treating physician. Therefore, the amount of TGFβ inhibitory and ECM degrading agents to be administered, as well as the number and timing of subsequent administrations, are determined, by a medical professional conducting therapy based on the response of the individual subject. Initially, such parameters are readily determined by skilled practitioners using appropriate testing in animal models for safety and efficacy, and in human subjects during clinical trials of candidate therapeutic formulations. Suitable animal models of human fibrotic conditions are known (see, e.g. Border and Noble, *New Eng. J. Med.* 331:1286–1292 (1994), incorporated by reference herein).

After administration, the efficacy of the therapy using the methods of the invention is assessed by various methods including biopsy of kidney, lung or liver or other tissue to detect the amount of extracellular matrix accumulated. An absence of significant excess accumulation of ECM, or a decrease in the amount or expansion of ECM in the tissue or organ will indicate the desired therapeutic response in the subject. Preferably, a non-invasive procedure is used to detect a therapeutic response. For example, changes in TGFβ activity can be measured in plasma samples taken before and after treatment with an inhibitor (see, Eltayeb et al., *J. Am. Soc. Nephrol.* 8:110A (1997)), and biopsy tissue can be used to individually isolate diseased glomeruli which are then used for RNA isolation. mRNA transcripts for TGFβ, and extracellular matrix components (e.g. collagen) are then determined using reverse transcriptase-polymerase chain reaction (RT-PCR) (Peten et al., *J. Exp. Med.* 176:1571–1576(1992)).

Advantages of the Invention

The invention provides improved treatment and prevention of fibrotic conditions associated with overproduction of TGFβ and excess accumulation of ECM in tissues and/or organs resulting in impaired function, or scarring, by reducing TGFβ overproduction directly and that resulting from multiple biological pathways, to effectively inhibit the TGFβ induced component of extracellular matrix deposition, and by increased degradation of ECM using degrading agents.

The therapeutic effects of the invention result from a reduction in or prevention of the TGFβ-induced excess accumulation of extracellular matrix in tissues and/or organs, and when combined with ECM degrading agents, from the increased degradation of ECM over time.

The following examples are presented to demonstrate the methods of the present invention and to assist one of ordinary skill in using the same. The examples are not intended in any way to otherwise limit the scope of the disclosure of the protection granted by Letters Patent granted hereon.

EXAMPLE I

Demonstration that Renin Upregulates TGFβ in Human Mesangial Cells

Normal fetal human mesangial cells (Clonetics Corp., Clonetics, Walkersville, Md.) passaged 5 to 8 times, were plated (3,000 cell/cm) in 12 well plates in 2 ml of medium (Mesangial Basal Medium (Clonetics Corp.) containing 5% FCS, 10 µg/ml penicillin and 100 µg/ml streptomycin) and allowed to grow to confluence for 48 hours at 37° C., 5% $CO_2$. Cultures were washed three times using sterile phosphate buffered saline at room temperature and then 2 ml/well of serum free MBM medium to induce quiescence. After 48 hours, the serum-free medium was removed and 2 ml/well of fresh serum-free medium was added. Human recombinant renin (Hoffman-La Roche Ltd., Basel, Switzerland) in concentrations from $10^{-6}$ to $10^{-12}$M was added to each well. A blank and 5 ng/ml of TGFβ (R & D Systems, Minneapolis, Minn.) were used as controls. Cells and supernatants were harvested by centrifugation after 24 hrs of culture and frozen at 10° C. until analysis. The total production and release of TGFβ into the culture supernatant was measured using an ELISA kit (R & D Systems). Induction of PAI-1 and fibronectin in the supernatant are also measured using anti-PAI-1 and anti-fibronectin antibodies in an ELISA to provide further confirmation of the inhibition of TGFβ. TGFβ, fibronectin and PAI-1 mRNA are measured using semi-quantitative RT-PCR.

(1) Determination of Dose Dependence of Renin Induction of TGFβ

Figure 2:
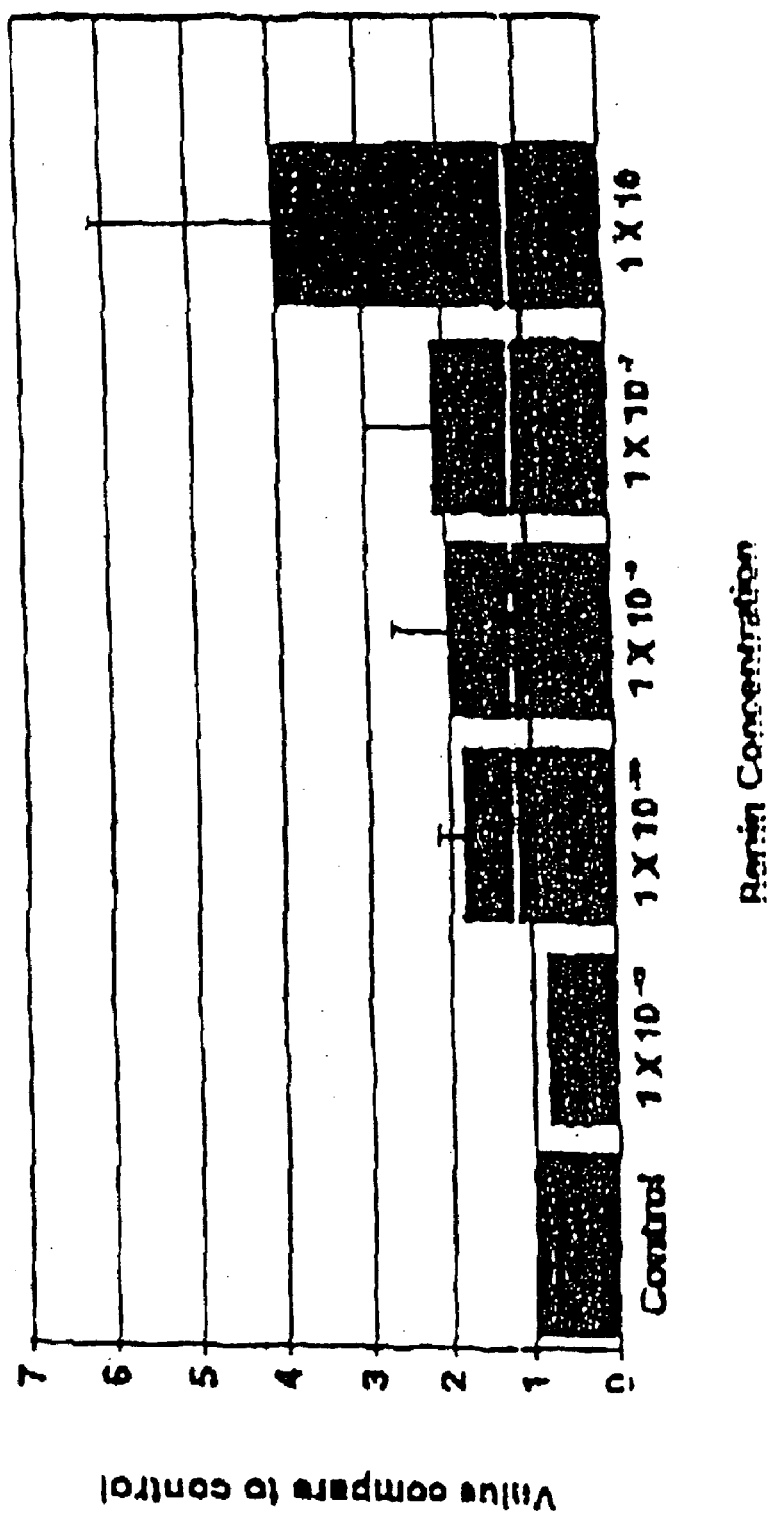
FIG. 2 is a bar graph showing increases in TGFβ production by cultured human mesangial cells in response to renin, as described in Example I, infra.

As shown in FIG. 2, renin increases the TGFβ production by cultured human mesangial cells in a dose-dependent manner.

EXAMPLE II

DEMONSTRATION OF THE EFFECT OF INHIBITING RENIN ON TGFβ PRODUCTION BY HUMAN MESANGIAL CELLS

Renin inhibitor Ro42-5892 (Hoffman-LaRoche, Basel, Switzerland), Losartan™ (Merck Pharmaceuticals, West Point, Pa.), Enalapril™ (Sigma Chemical Co., St. Louis, Mo., Prod. No. E6888), or TGFβ1 neutralizing antibody (R & D Systems) were added in the amounts indicated below to separate wells in triplicate to block the renin cascade at different sites after stimulation by renin:

$10^{-5}$M Renin Inhibitor Ro 42-5892 (Hoffman-LaRoche)

30 ng/ml Anti-TGFβ1 antibody (R & D Systems, #AB 101 NA)

30 ng/ml Chicken IgG (control for anti-TGFβ1 antibody, R & D Systems, # AB 101 C)

$10^{-5}$M Enalapril™ (Sigma Chemical Co., St. Louis, Mo.)

$10^{-5}$M Losartan (Merck Pharmaceuticals, West Point, Pa.)

These inhibitors were added at zero time with $10^{-7}$M human recombinant renin (Hoffman-LaRoche).

Figure 3:
FIG. 3 is a bar graph showing the effect of blocking agents on TGFβ-production by human mesangial cells in response to renin, as described in Example II, infra.

As shown in FIG. 3, use of inhibitors that block renin's action to increase Angiotensin II i.e. blocking Angiotensin I production from Angiotensinogen (Ro 42-5892), blocking Angiotensin I conversion to Angiotensin II (Enalapril™) and blocking binding of Angiotensin II to its type 1 receptor (Losartan™), does not reduce the renin-induced increase in TGFβ production. These results demonstrate for the first time an alternative pathway in which TGFβ production is stimulated by renin.

EXAMPLE III

Demonstration of Inhibition of TGFβ by Blocking Renin In Vivo in the Presence of an Anti-Fibrotic Drug In this example, a known fibrotic disease drug, Enalapril™ which inhibits the production of Angiotensin II, is combined with an inhibitor of renin, antisense renin oligonucleotide, to obtain an enhanced therapeutic effect on fibrotic disease in an animal model.

Rats are administered Enalapril™ in their drinking water prior to anti-thymocyte serum injection, e.g. three (3) days prior to injection. Anti-thymocyte antibody, e.g. OX-7, is injected intravenously into the rats at day three to produce fibrotic disease. (Bagchus et al., *Lab. Invest.* 55:680–687 (1986)). Renin antisense oligonucleotides are administered one hour following administration of OX-7 by introducing the oligonucleotides into a suitable vehicle, such as HVJ liposomes, and injecting the formulations into the left renal artery of Sprague Dawley rats as described for renin genes by Arai et al., *Biochem. And Biophys. Res. Comm.* 206(2):525–532 (1995), incorporated by reference herein. A control consisting of nonsense encoding oligonucleotides (e.g. derived from the renin antisense gene sequence) is also injected into the left renal artery of additional rats. The renin antisense localizes in the juxtaglomerular apparatus of the glomerulus where renin is produced blocking renin production.

Animals are sacrificed on day 7 and kidney tissue samples are taken for analysis of levels of TGFα in the glomeruli. Glomeruli are sieved individually from each rat and placed in culture in suitable medium for three days. At the end of culture, culture supernatant, is harvested by centrifugation and TGFβ, fibronectin and PAI-1 production are determined as makers of fibrotic renal disease severity. Other glomeruli are pooled and used to isolate RNA. RNA is used by standard methods to quantitate expression of mRNAs of interest, including TGFβ, fibronectin and collagens.

Glomeruli are also examined histologically for phenotypical changes, e.g. changes resulting from deposition for ECM. Phenotypic changes are associated with pathological alteration of glomeruli indicative of fibrotic disease. Such changes include expansion of extracellular matrix in the mesangial area of the kidney in animal models and the presence of activated mesangial cells which have acquired the characteristics of fibroblasts, e.g. expressing α-smooth muscle actin and interstitial collagen, indicating progressive glomerular injury (Johnson et al., *J. Am. Soc. Nephrol.* 2:S190–S197 (1992)). Tissue for light microscopy is fixed in formaldehyde, then dehydrated in graded ethanol and embedded in paraffin. Sections are cut at 3 µm thickness and are stained with with the periodic Schiff reagent. The paraformaldehyde-fixed renal section of the rats are also incubated with mouse anti-human renin monoclonal antibody (Kaiichi Radioisotope Labs, Ltd., Tokyo, Japan), mouse anti-α-smooth muscle actin monoclonal antibody (Immunotech S. A. (Marseille, France) and rabbit anti-collagen antibodies (Chemicon, Temicula, Calif., prod. No. AB755). The sections are further processed using Vectastain ABC Kit (Vector Laboratories, Inc., Burlingame, Calif.).

Results of antibody binding indicate the extent of glomerular injury and the effects of inhibition of renin on such injury.

EXAMPLE IV

Additional Demonstration that Renin Upregulates TGFβ in Human Mesanglil Cells

Primary cultures of adult human mesangial cells were grown from human nephrectomy tissues using standard methods. Cells were passaged 4–7 times and then plated (3,000 cell/cm2) in 12 well plates in 2 ml of medium (Mesangial Basal Medium (Clonetics Corp, containing 5% FCS, 10 µg/ml penicillin and 100 µg/ml streptomycin) and allowed to grow to 70% confluency for 48 hours at 37° C., 5% $CO_2$. Cultures were washed three times using sterile phosphate buffered saline at room temperature and then 2 ml/well of serum free MBM medium to induce quiescence. After 48 hours, the serum-free medium was removed and 2 ml/well of fresh serum-free medium was added for 24 hours. Human recombinant renin (HrRenin, Hoffman-La Roche Ltd., Basel, Switzerland) in concentrations from $10^{-6}$ to $10^{-12}$M was added to each well for 24 hours. A blank (no HrRenin) was used as a control. Cells and supernatants were harvested by centrifugation after 24 hrs of culture and frozen at 70° C. until analysis.

The total production and release of TGFβ into the culture supernatant was measured using an ELISA kit (R & D Systems). Induction of the matrix protein fibronectin (Fn) in the supernatant was measured using anti-fibronectin antibodies in an ELISA to provide further confirmation of induction of TGFβ. Renin-induced induction of TGFβ, fibronectin and PAI-1 mRNA were measured over time using semi-quantitative RT-PCR in a multiple# system where multiple cDNAs are amplified simultaneously according to Dostal et al., *Anal. Biochem.* 223:239–250 (1994), incorporated by reference herein Determinations were done in triplicate mesangial cell cultures.

(1) Determination of Dose Dependency of Renin Induction of TGFβ

Figure 4:
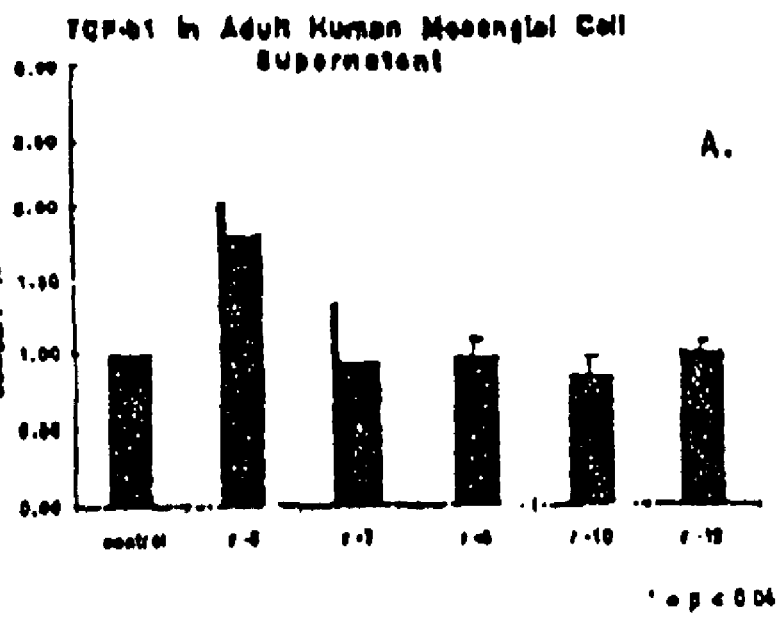
FIGS. 4A and B are bar graphs showing dose dependent increases in TGFβ (FIG. 4A) and Fn production (FIG. 4B) with increases in HrRenin as described in Example IV, infra.
Figure 4:
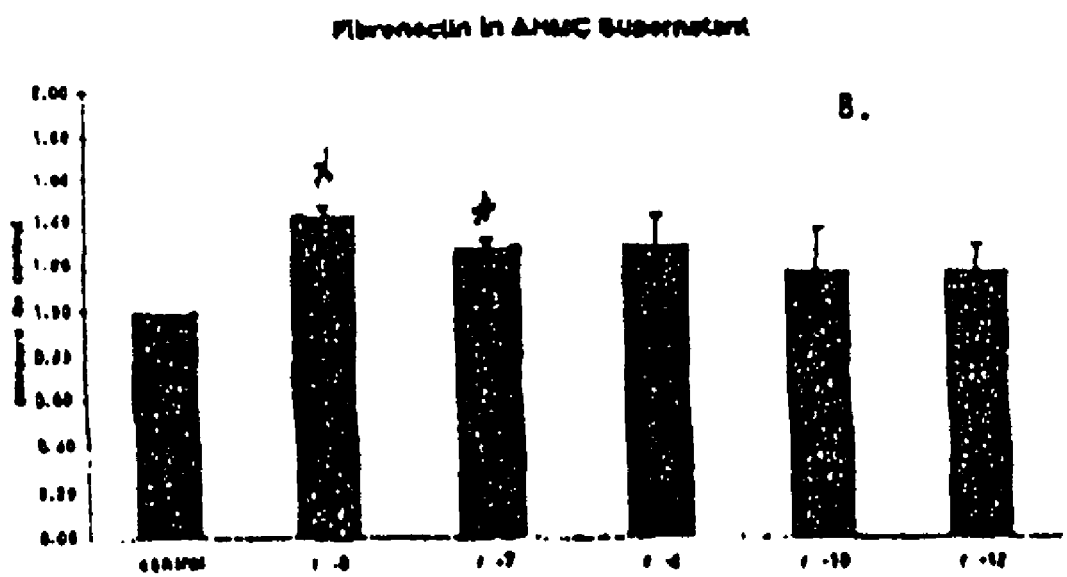
Figure 5:
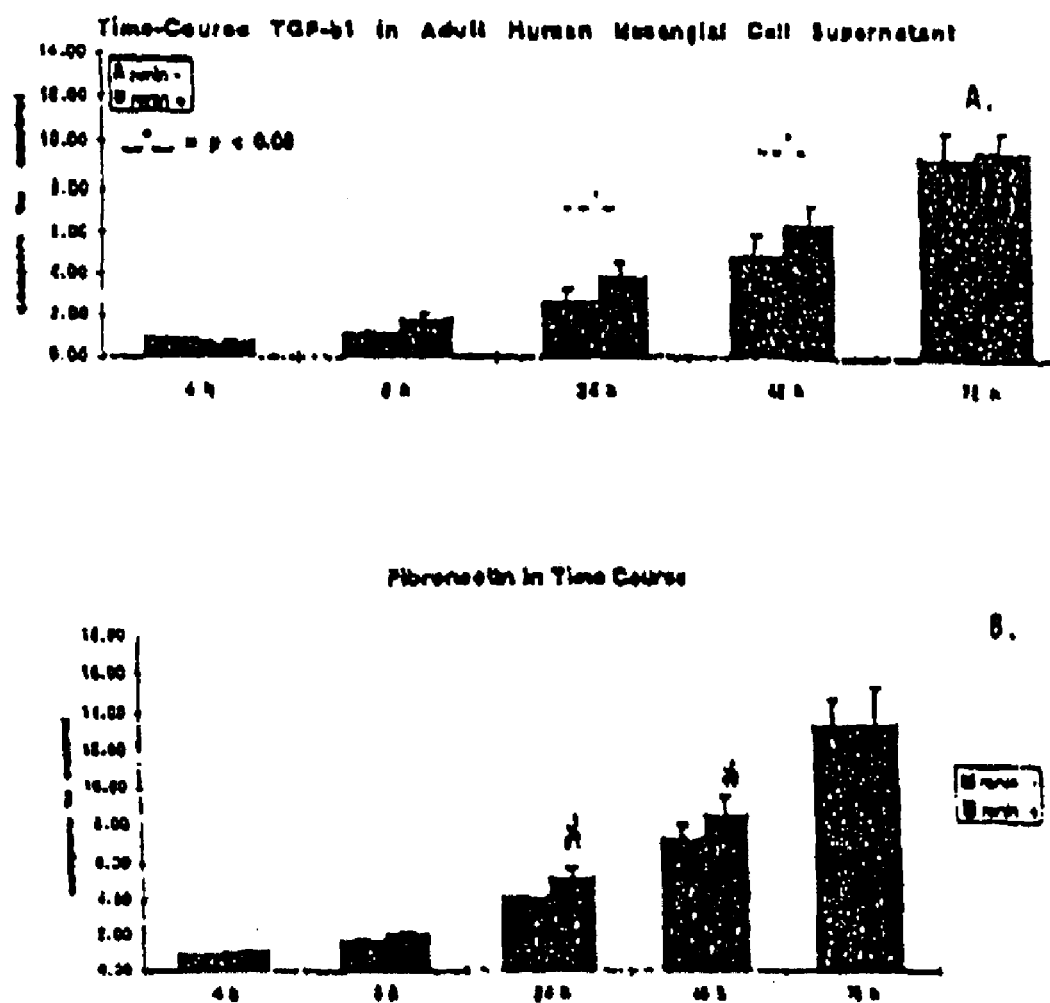
FIGS. 5A and B are bar graphs showing time courses of TGFβ (FIG. 5A) and Fn production (FIG. 5B) as described in Example IV, infra.
Figure 6:
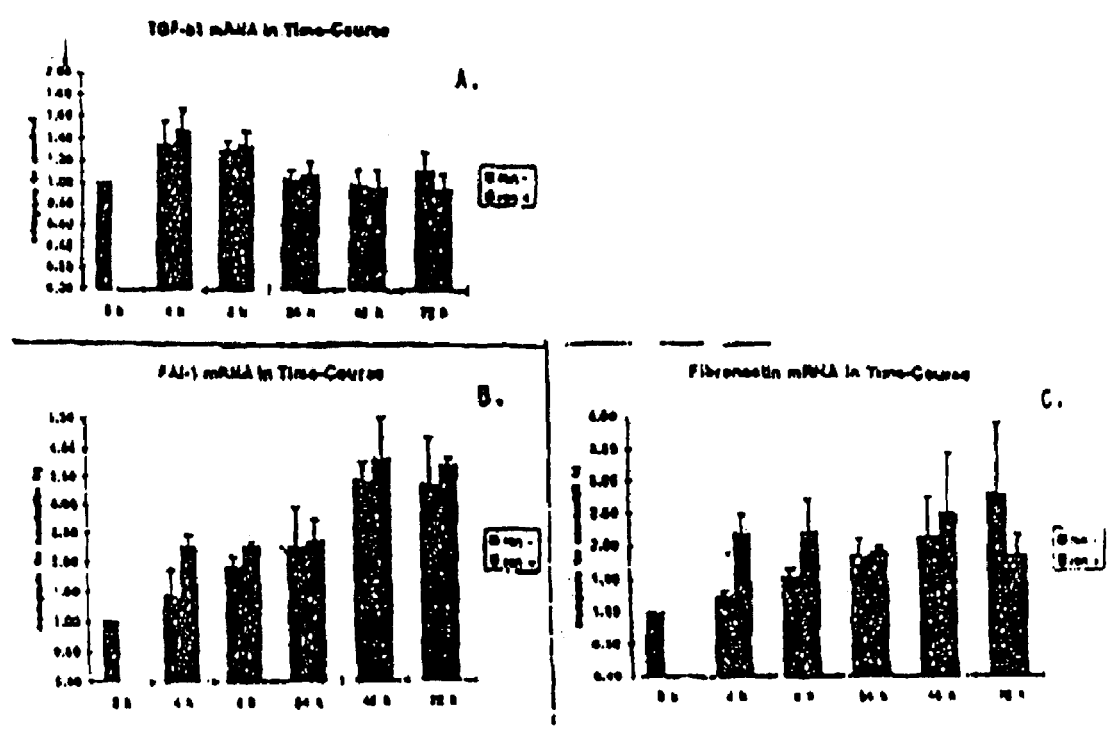
FIGS. 6A–C are bar graphs showing renin-induced increases in TGFβ, PAI-1 and Fn mRNAs over time as described in Example IV, infra.

As shown in FIG. 4, statistically significant (p<0.05) dose dependent increases in TGFβ (FIG. 4A) and Fn production (FIG. 4B) were observed, peaking with 2- and 1.4-fold increases at $10^{-6}$M HrRenin, respectively. Time course experiments using $10^{-7}$M HrRenin revealed significant increases in TGFβ and Fn production at 24 and 48 hours (p<0.03 (FIGS. 5A and B). As shown in FIGS. 6A–C, renin-induced increases in TGFβ, PAI-1 and Fn mRNAs peaked at 4 hours with increases from 1.5- to 2-fold.

(2) Demonstration that Renin Upregulation of TGFβ is not Mediated Through Renin Enzymatic Activity or Angiotensin II Renin inhibitor Ro42-5892 (Hoffman-LaRoche, Basel, Switzerland), Losartan™ (Merck Pharmaceuticals, West Point, Pa.), Enalapril™ (Sigma Chemical Co., St. Louis, Mo., Prod. No. E6888), or TGFβ1 neutralizing antibody (R & D Systems) were added in the amounts indicated below to separate wells in triplicate to block the renin cascade at different sites after stimulation by renin:

$10^{-5}$M Renin Inhibitor R042-5892 (Hoffman-LaRoche)
$10^{-5}$M Enalapril™ (Sigma Chemical Co., St. Louis, Mo.)
$10^{-5}$M Losartan (Merck Pharmaceuticals, West Point, Pa.)
Controls included neutralizing antibody to TGFβ (ATG) and control IgG (TgG)

These inhibitors were added at zero time with $10^{-7}$M human recombinant renin (Hoffman-LaRoche).

Figure 7:
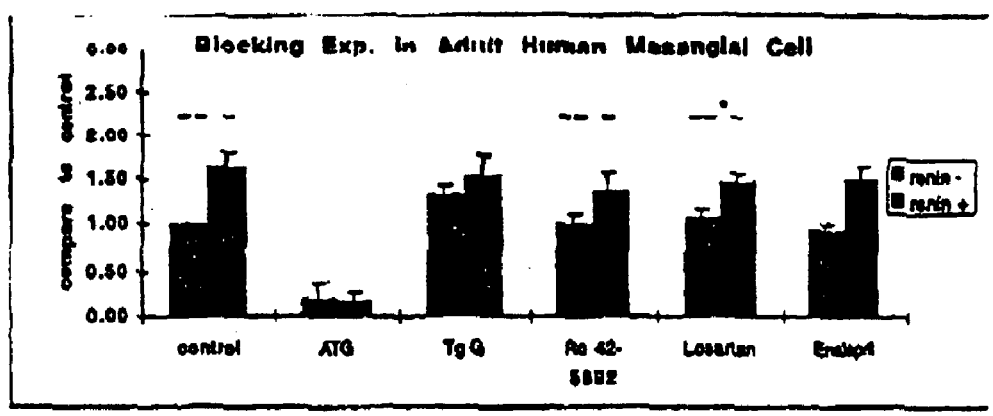
FIG. 7 is a bar graph showing the results of inhibitors that block renin's action to increase Angiotensin II, on the renin-induced increase in TGFβ production in adult human mesangial cells as described in Example IV, infra.

As shown in FIG. 7, use of inhibitors that block renin's action to increase Angiotensin II, i.e. blocking Angiotensin I production from Angiotensinogen (RO 42-5892), blocking Angiotensin I conversion to Angiotensin II (Enalapril™) and blocking binding of Angiotensin II to its type I receptor (Losartan™), does not reduce the renin-induced increase in TGFβ production.

These results provide additional evidence that renin upregulates TGFβ production by human mesangial cells through a mechanism which is independent of renin's enzymatic action to convert angiotensin to Angiotensin I, and independent of Angiotensin II generation. These results may have profound implications for progression of fibrotic renal disease, particularly in states of high plasma renin as are observed with therapeutic Angiotensin II blockade. Thus, the use of therapeutic agents such as Enalapril™ or Losartan™ for Angiotensin blockade may not be optimal as treatment agents because of resulting high renin levels, preventing a therapeutic reduction in TGFβ. In addition, antagonists developed to block the site on renin that acts in the Angiotensin II pathway, would not be expected to block the action of renin that is independent of this pathway. Therefore, effective therapy of fibrotic diseases must take these multiple pathways for TGFβ increase into consideration.

EXAMPLE V

Demonstration of the Ability of tPA to Increase Plasmin Degradation of Accumulated ECM In Vivo In this Example, recombinant tissue type plasminogen activator (rtPA) was shown to promote generation of the protease plasmin in nephritic glomeruli and to degrade pathological ECM proteins leading to a therapeutic reduction in matrix accumulation.

Six Sprague-Dawley rats with were injected with phosphate buffered saline (PBS, as a control) and 18 rats were injected with 300 ug of mouse monoclonal OX7 antibody produced in the laboratory using commercially obtained hybridoma cells (American Type Culture Collecton (Rockville, Md., USA; Peters et al., Kidney Internatl. 54:1570–1580 (1998)) on day 1 to induce anti-Thy-1 nephritis. Injection of the anti rat-thymocyte antibody intravenously causes binding to an epitope in rat glomerular mesangial cells call Thy 1.1. The complement-mediated mesangial cell lysis that follows initiates a cascade of tissue injury, followed by a repair process that involves induction of TGFβ-driven production and deposition of ECM components. In addition, the plasmin protease system is altered such that PA is decreased and PAI-1 is markedly increased. These alterations favor decreased plasmin generation which decreases matrix turnover and enhances matrix accumulation. Plasmin is the key to mesangial cell matrix turnover (Baricos et al, Kidney Int. 47:1037–1047 (1995)).

Three days after the initial injection, rtPA (Genentech, Inc., San Francisco, Calif.) in a formulation designed for rodent intravenous injection (GenBank E08757) or PBS was injected intravenously. Injections were repeated twice a day from day 3 to day 5. RtPA was injected i.v. at a dose of 1 mg/kg BW (n=6). Controls received saline (n=6). Glomerular staining for ECM matrix proteins (collagen type I and III, fibronection EDA+ and tenascin) and glomerular mRNA levels of TGFβ1, fibronectin and PAI-1 were evaluated at day 6. Localization of rtPA in nephritic glomeruli and the effect of rtPA on glomerular plasmin were investigated. Rats were sacrificed at day 6 and kidney tissues excised, fixed in formalin and frozen for histological analysis.

TABLE 1

| Groups of Six Rats | Treatment |
| --- | --- |
| Group 1 - Normal controls | 300 ug of PBS on day 1, then 300 ug PBS 2X |
| Group 2 - Disease control | 300 ug of OX7 on day 1, then 300 ug PBS 2X |
| Group 3 - Disease + Dose 1 | 300 ug of OX7 on day 1, then 0.25 mg/day rtPA 2X/day on days 3, 4 and 5 |

Kidney tissue sections were stained for extracellular matrix using Periodic Acid Schiff (PAS) using standard procedures and were stained for specific relevant matrix proteins such as Collagen 1, Collagen IV, Fibronectin EDA and tenascin using standard immunohistochemical staining procedures, Matrix proteins were scored by image analysis of 30 glomeruli per rat.

Figure 8:
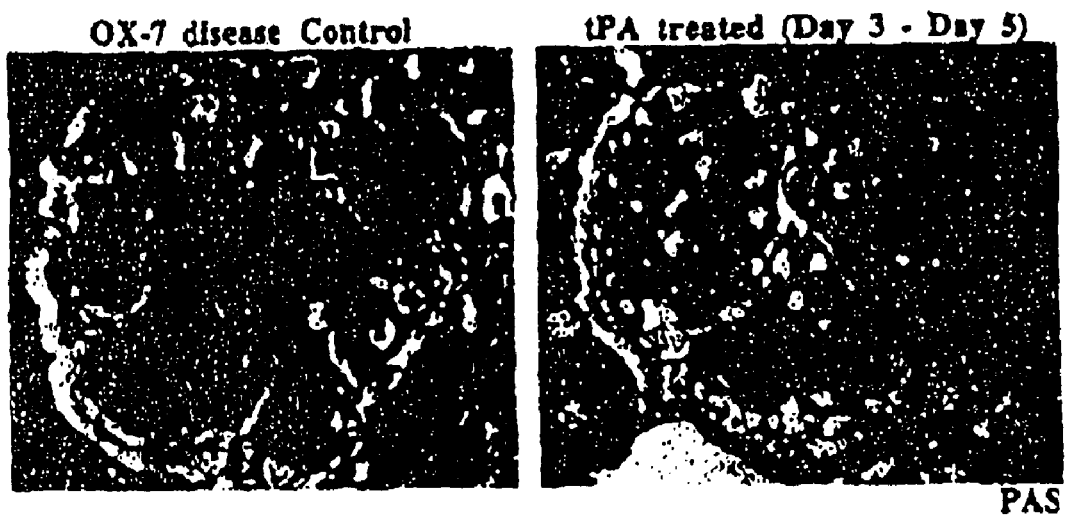
FIGS. 8A and B are photographs depicting the effects of tPA treatment on ECM accumulation in glomeruli as described in Example V, infra.
Figure 9:
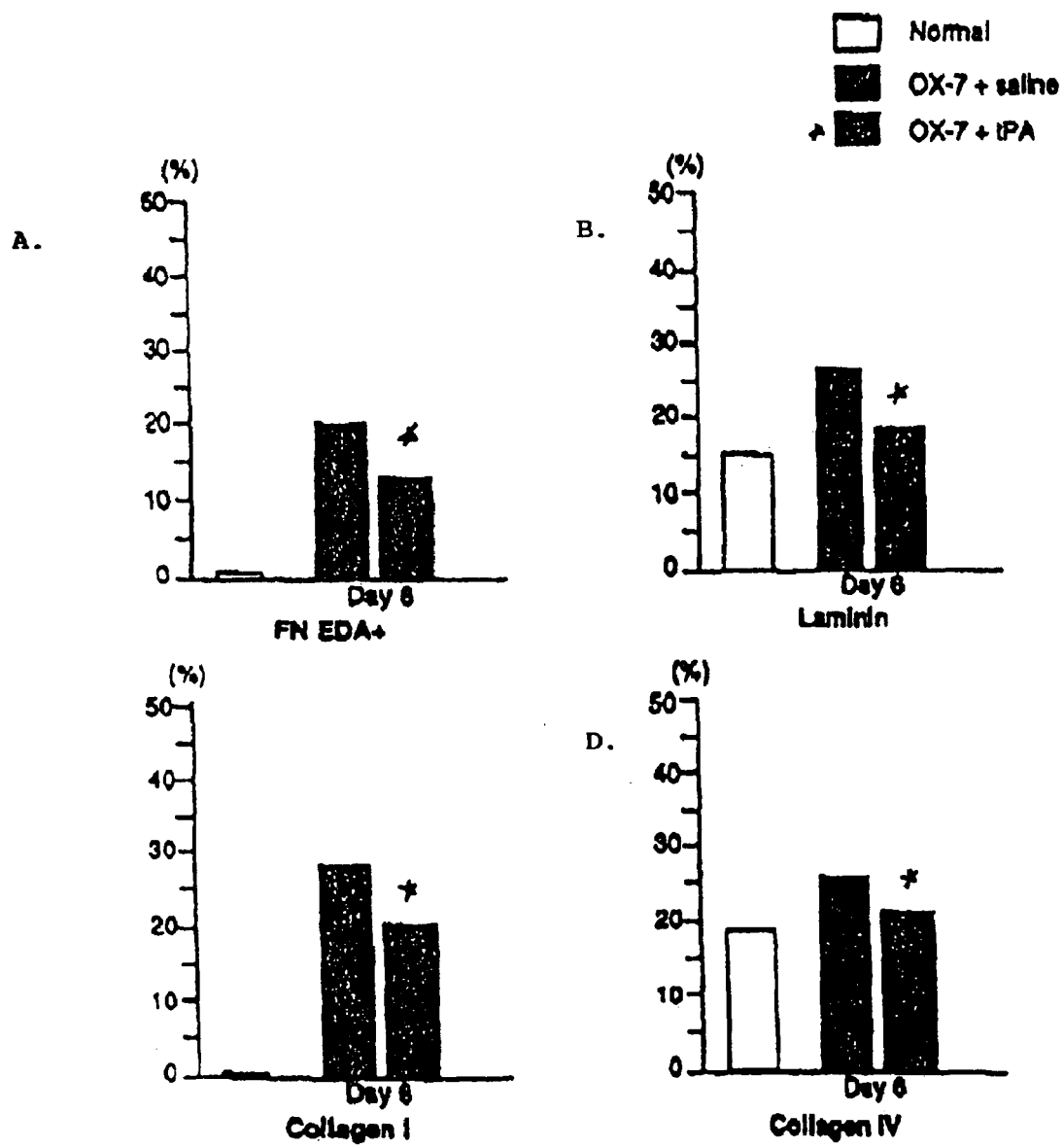
FIGS. 9A–D are bar graphs depicting the effects of tPA treatment on amounts of ECM constituents (9A: FN EDA+; 9B: Laminin; 9C: Collagen I and 9D: Collagen IV) as determined by staining as described in Example V, infra.
Figure 10:
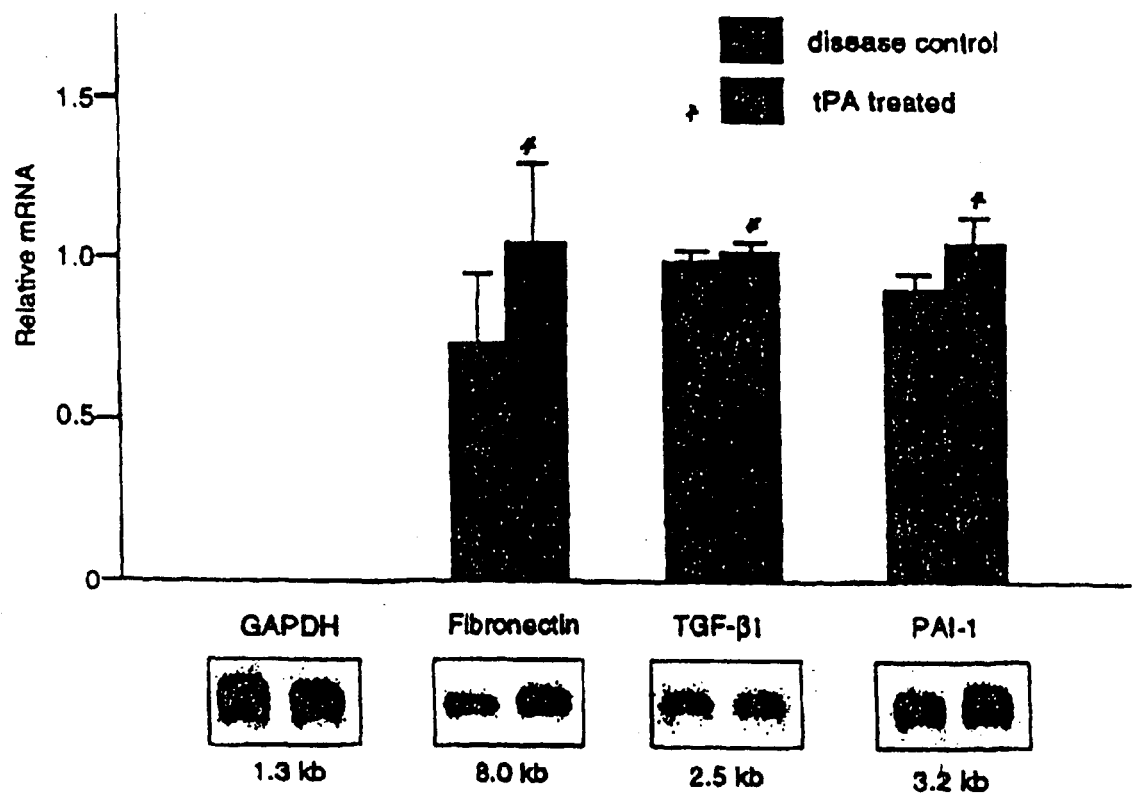
FIG. 10 is a bar graph showing the effects of tPA on glomerular mRNA expression at day 6 as described in Example V, infra.
Figure 11:
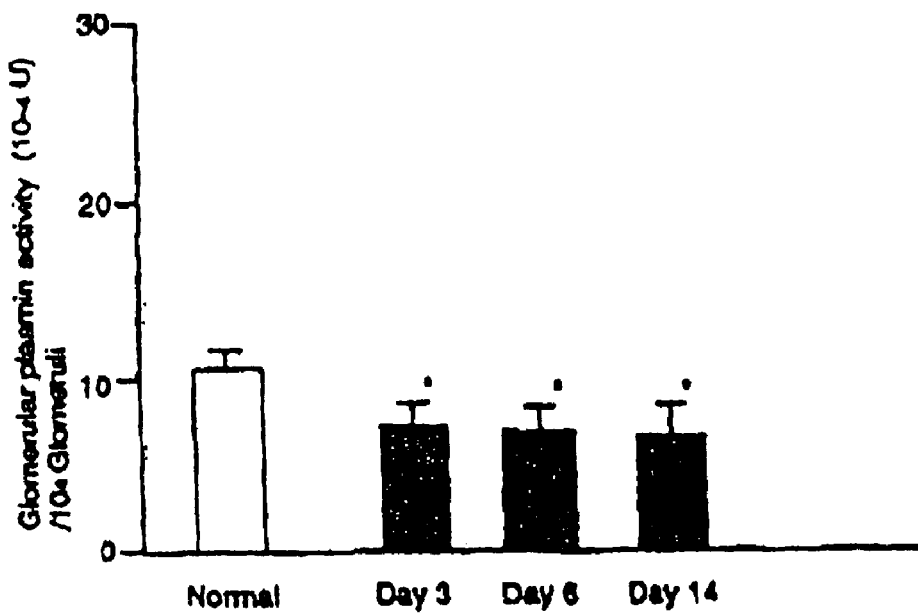
FIGS. 11A and B are bar graphs showing the effects of tPA treatment on glomerular plasmin activity as described in Example V, infra.
Figure 11:
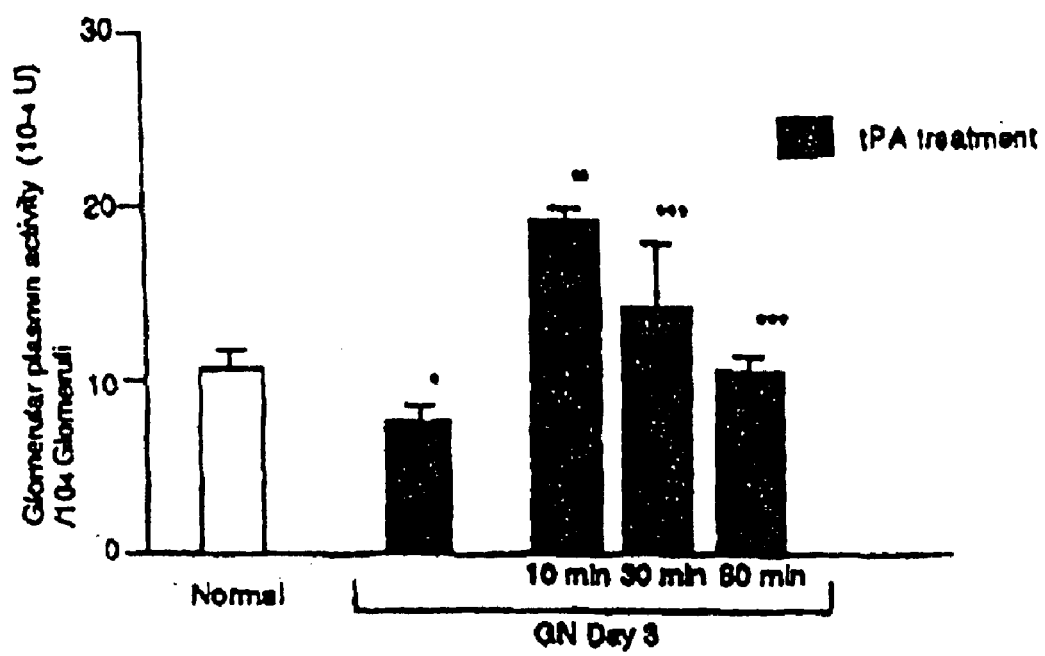

FIGS. 8A (control) and B (tPA) show an overall decrease in matrix accumulated as a result of tPA treatment. Compared to the untreated, disease control group (FIGS. 9A–D), the percentage of the glomerular area with positive staining was significantly lower in the rtPA treated group at day 6 for fibronectin EDA+(FN)(19±2 vs. 14±1, p<0.01), laminin (35±2 vs. 25±2, p<0.001), type I collagen 33±1 vs. 21±3, p<0.001) and type IV collagen (27±2 vs. 23 ±1, p<0.01). Glomerular levels of TGFβ1, FN and PAI-1 mRNA were unchanged (FIG. 10). rtPA co-localized with fibrin along the glomerular capillary loops and in the mesangium.

rtPA was injected into nephritic rats 10, 20 and 30 minutes before sacrifice. At sacrifice, glomeruli were isolated and placed in culture with a chromogenic substrate for tPA. Plasmin generation by nephritic glomeruli, as shown in FIG. 11, was significantly elevated in tPA treated nephritic glomeruli compared to nephritic gomeruli from disease control rats.

This example demonstrates that injected rtPA binds fibrin in nephritic glomeruli where it increases plasmin generation and promotes pathological ECM degradation. rtPA may thus be used in the methods of the invention as an ECM degrading agent.

EXAMPLE VI

Effect of Administration of TGFβ Inhibitory Agents and Agents that Promote Degradation of ECM In this example, at least one agent that inhibits TGFβ, anti-TGFβ antibody or decorin, is administered in combination with an ECM degrading agent, such as rtPA to reduce excess ECM accumulation and degrade accumulated ECM in an animal model of glomerulonephritis.

Sprague-Dawley rats are treated as described in the above Examples to induce nephritis. Groups of six (6) rats each include untreated disease controls, rats treated with tPA alone as in Example V, above, rats treated with Enalapril™ alone (200 mg/day) in drinking water and rats treated with both intravenous rtPA and Enalapril™ in drinking water. On day 6 rats are sacrificed and kidney sections are excised, fixed in formalin and frozen for histological analysis. Glomeruli are isolated and used for in vitro analysis of production of TGFβ, fibronectin and PAI-1 using ELISA assays of culture supernatants and for isolation of RNA for Northern analysis of message levels of TGFβ, fibronectin and PAI-1. Tissue samples are stained for ECM proteins and glomerular mRNA levels of TGFβ1, fibronectin and PAI-1.

It is expected that the results of treatments with both anti-TGFβ antibody and rtPA treatment are significantly lower positive staining both in PAS stained tissue and in glomeruli stained for specific matrix components, as shown in Example V, compared with groups treated with either agent alone or in the control disease group.

EXAMPLE VII

Demonstration of the Effects of Administration of a PAI-1 Mutant on Extracellular Matrix Degradation The human PAI-1 mutant used in this experiment (see WO 97/39028); was constructed on the wild-type PAI-1 background (Ginsburg et al., J. Clin. Invest 78:1673–1180 (1986)), and disabled by the introduction of two Arg residues at positions 333 and 335 of the mature protein, which are also referred to as residues P14 and P12 of the reactive center loop (Lawrence, Adv. Exp. Med. Biol. 425:99–108 (1997)). Upon interaction with a proteinase, these substitutions greatly retard the insertion of the reactive center loop into β-sheet A and prevent the mutant from adopting the latent conformation. Since loop insertion results in loss of vitronectin affinity (Lawrence et al., 1997, supra), the PAI-1 mutant retains significant vitronectin activity while failing to inhibit all plasminogen activators.

Four to six week old male Sprague-Dawley rats (Sasco, Inc., Omaha, Nebr.) were treated as described in the above Examples to induce anti-thy-1 nephritis by intravenous injection of the monoclonal anti-thymocyte antibody OX-7 350 mg/200 g body weight. Groups of six (6) rats included a normal control group (injected with saline), an untreated disease control group (injected with PBS), and a group treated with 1 mg/Kg PAI-1 mutant injected once a day beginning 24 hours after induction of ATS nephritis and ending at day 5. Two additional groups of rats were treated with 1) 100 mg/liter of Enalapril (in drinking water) with a loading dose of Enalapril given by gavage 24 hr after disease induction followed by 100 mg/liter of Enalapril in drinking water, and 2) a 6% low protein diet (Teklad, Madison, Wis., diet number TD86551) started 24 hours following disease induction.

Rats were sacrificed at day 6 and kidney tissues excised, fixed in formalin and frozen for histological analysis. Kidneys were perfused in situ with cold buffered saline (PBS) at pH 7.4, and then excised. Pieces of cortex were removed and either snap frozen in 2-methylbutane that had been cooled in liquid nitrogen or fixed in 10% neutralized formalin for immunohistologic examination. The capsules were removed and the cortical tissue dissected out and minced with a razor blade prior to isolation of glomemli by standard graded seiving. Kidney tissue sections were stained for extracellular matrix using Periodic Acid Schiff(PAS) using standard procedures and were stained for specific relevant matrix proteins such as Collagen I, Collagen IV, Fibronectin EDA and tenascin using standard immunohistochemical staining procedures. Matrix proteins were scored by a blinded observer. 20 glomeruli per rat were evaluated. Isolated glomeruli were also used to determine glomerular mRNA levels of TGFβ1, fibronectin and PAI-1 at day 6.

Reagents to measure plasmin activity, including plasminogen, low molecular weight u-PA and H-D-Val-Leu-Lys-p-nitroanilide (S-2251) were obtained from KabiVitrum (Franklin, Ohio). PAI-1 activity was assayed by measuring the hydrolysis of synthetic substrate by formed plasmin in the presence of plasminogen (Marshall et al., *J. Biol. Chem.* 265:9198–8204 (1990)). Assays were performed in polyvinyl chloride microtiter plates. The total volume of 125 μl was comprised of the following: sample, H-D-Val-Leu-Lys-P-nitroanilide (0.01 μM) and plasminogen (0.03 μM) in 0.5% Triton X-100, 0.1M Tris, at pH 8.0. The amount of p-nitroaniline released was measured at 410 nm with a Thermomax microplate reader (Molecular Devices, Menlo Park, Calif.). A standard curve was generated with each assay using low molecular weight human u-PA. Each sample was also assayed without plasminogen to establish the plasminogen dependence of the enzyme activity. The plasmin activity in culture supernatant or cell lysate was expressed as IU/1000 glomeruli.

Figure 12:
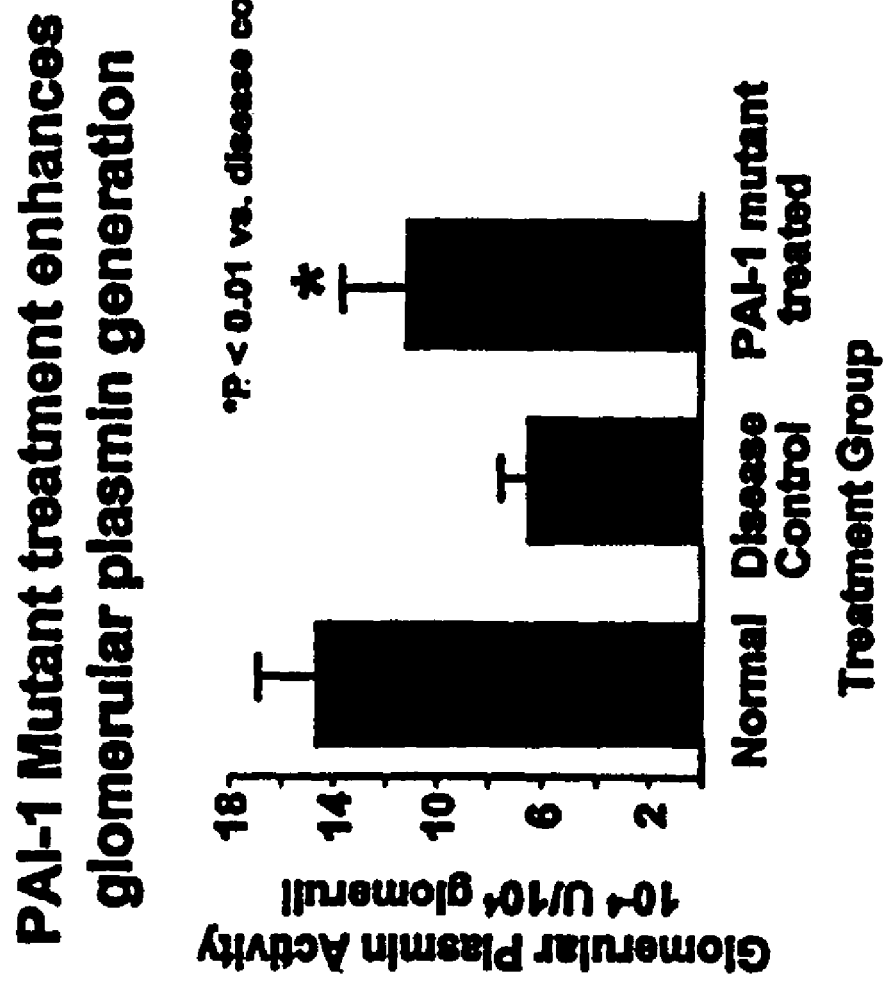
FIG. 12 is a bar graph demonstrating that injection of PAI-1 mutant results in increases in plasmin generation of nephritic glomeruli, as described in Example VII, infra.

FIG. 12 shows an increase in plasmin generation of glomeruli in culture as a result of injection of the PAI-1 mutant. Compared to the untreated, disease control group, the glomerular plasmin activity was significantly higher in the PAI-1 treated group, being approximately halfway between the activity of disease controls and normal glomeruli. Notably, the significant increase in glomerular plasmin activity in nephritic glomeruli was observed with the PAI-1 mutant 24 hours following the final injection.

Figure 13:
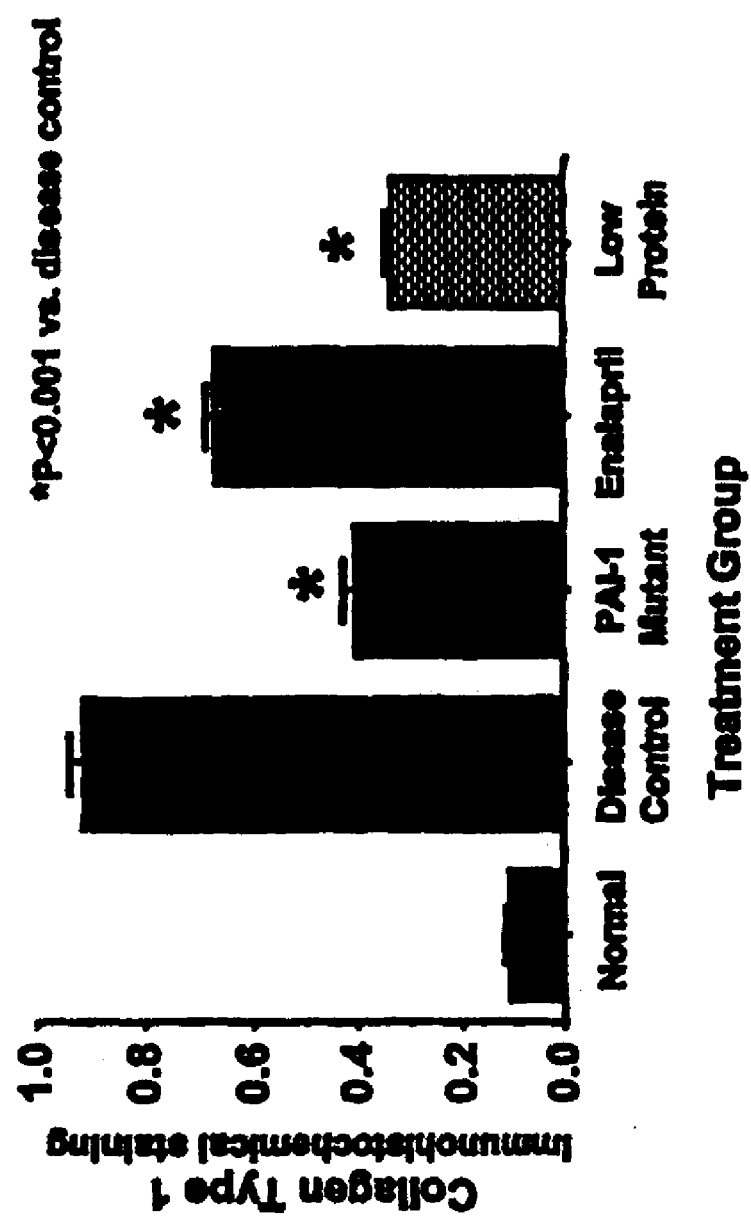
FIG. 13 is a bar graph demonstrating decreased accumulation of Collagen type I after administration of PAI-1 mutant, as described in Example VII, infra.

In addition, treatment with the PAI-1 mutant resulted in decreased accumulation of Collagen Type I, relative to diseases controls (FIG. 13), while glomerular levels of TGFβ1, FN, PAI-1 mRNA and Collagen I mRNA were not significantly altered. The decreased accumulation of Collagen Type I together with the fact that the Collagen I mRNA does not significantly decrease suggests enhanced extracellular matrix degradation rather than decreased production of Collagen I.

These results suggest that the increase in glomerular plasmin activity with a PAI-1 mutant can be titrated to avoid large increases in plasmin generation that may lead to hemorrhaging. Thus, the dose of the PAI-1 mutant may be altered, for example by doubling the dose, increase glomerular plasmin activity to normal, but not excessive, levels to decrease deleterious accumulation of extracellular matrix. In addition, the time of treatment may be extended, for example to 10 days to obtain desired degradation.

Various publications are cited herein that are hereby incorporated by reference in their entirety.

As will be apparent to those skilled in the art in which the invention is addressed, the present invention may be embodied in forms other than those specifically disclosed without departing from the spirit or potential characteristics of the invention. Particular embodiments of the present invention described above are therefore to be considered in all respects as illustrative and not restrictive. The scope of the invention is as set forth in the appended claims and equivalents thereof rather than being limited to the examples contained in the foregoing description.

What is claimed:

1. A method for treating a condition associated with the excess accumulation of extracellular matrix in a tissue and/or organ or at a dermal wound site comprising:
    a) reducing the excess accumulation of extracellular matrix associated with TGFβ overproduction and/or activity in an organ or tissue, or at a wound site, by administering in an amount sufficient to inhibit TGFβ overproduction and/or activity, a first agent that reduces TGFβ-associated accumulation of extracellular matrix; and
    b) degrading excess accumulated extracellular matrix in said tissue and/or organ or wound site, by administering in an amount sufficient to degrade excess accumulated extracellular matrix, a different, second agent that degrades extracellular matrix;
    whereby the accumulation of extracellular matrix in said tissue and/or organ or wound site is reduced from the level existing at the time of treatment.

2. The method of claim 1 wherein the accumulation of extracellular matrix is reduced to a level which does not interfere with normal functioning of the tissue or organ or result in scarring.

3. The method of claim 1 wherein said first agent that reduces TGFβ-associated accumulation of extracellular matrix is selected from the group consisting of inhibitors of aldosterone, inhibitors of angiotensin II, anti-TGFβ antibodies, renin, ACE inhibitors, AII receptor antagonists, proteoglycans and ligands for the TGFβ receptor.

4. The method of claim 3 wherein said ACE inhibitor is Enalapril™.

5. The method of claim 1 wherein said step of degrading excess accumulated extracellular matrix comprises contacting said matrix with at least one protease in an amount sufficient to degrade excess accumulated extracellular matrix to a level that does not impair the normal function of said tissue and/or organ or result in scarring.

6. The method of claim 5 wherein said at least one protease is selected from the group consisting of serine proteases, metalloproteinases and protease combinations.

7. The method of claim 1 wherein said step of degrading accumulated extracellular matrix comprises administering an agent which increases the amount of active protease sufficient to degrade excess accumulated matrix to a level that does not impair the normal function of said tissue and/or organ or result in scarring.

8. The method of claim 7 wherein said protease is selected from the group consisting of serine proteases, metalloproteinases and protease combinations.

9. The method of claim 8 wherein said protease is plasmin and said agent which increases the amount of active plasmin is tPA.

10. The method of claim 1 wherein said condition associated with the excess accumulation of extracellular matrix is a fibrotic condition.

11. The method of claim 10 wherein said fibrotic condition is selected from the group consisting of glomerulonephritis, adult or acute respiratory distress syndrome (ARDS), diabetes, diabetic kidney disease, liver fibrosis, kidney fibrosis, lung fibrosis, post infarction cardiac fibrosis, fibrocystic diseases, fibrotic cancer, post myocardial infarction, left ventricular hypertrophy, pulmonary fibrosis, liver cirrhosis, veno-occlusive disease, post-spinal cord injury, post-retinal and glaucoma surgery, post-angioplasty restenosis, renal interstitial fibrosis, arteriovenous graft failure and scarring.

12. The method of claim 1 wherein said tissue or organ is selected from the group consisting of kidney, lung, liver, heart, arteries, skin and the central nervous system.

13. The method of claim 1 wherein said condition associated with the excess accumulation of extracellular matrix is scarring.

14. The method of claim 1 wherein said first agent that reduces TGFβ-associated accumulation of extracellular matrix is nucleic acid encoding the agent.

15. The method of claim 5 wherein said protease is nucleic acid encoding a protease.

16. The method of claim 1, wherein said first agent that reduces TGFβ-associated accumulation of extracellular matrix and said second agent that degrades excess accumulated extracellular matrix are administered concurrently.

17. The method of claim 1 wherein said first agent that reduces TGFβ-associated accumulation of extracellular matrix and said second agent that degrades excess accumulated extracellular matrix are administered sequentially.

18. A method for treating a condition associated with the excess accumulation of extracellular matrix in a tissue and/or organ, or at a wound site, comprising administering in an amount sufficient to inhibit TGFβ activity and/or production, a combination of at least one first agent and at least one second agent, to prevent or reduce the excess accumulation of extracellular matrix associated with TGFβ overproduction in a tissue and/or organ, or at a wound site, said first agent an agent that reduces TGFβ-associated accumulation of extracellular matrix, and said second agent an agent that degrades extracellular matrix.

19. The method of claim 18 wherein said agents are nucleic acids encoding said at least one first agent and at least one second agent.

20. The method of claim 18 wherein said agents are administered to reduce TGFβ overproduction prior to excess accumulation of extracellular matrix.

* * * * *